US010111975B2

(12) United States Patent
Laflamme et al.

(10) Patent No.: US 10,111,975 B2
(45) Date of Patent: Oct. 30, 2018

(54) STERILIZATION METHODS AND APPARATUS AND ADAPTIVE CONTROL THEREOF

(71) Applicant: TSO3 INC., Quebec (CA)

(72) Inventors: Jonathan Laflamme, Quebec (CA); David Sohier, Quebec (CA); Sylvie Dufresne, Quebec (CA); Cecile Chevalier, Montreal (CA); Helene Leblond, Quebec (CA); Francis Therrien, St-Sebastien (CA)

(73) Assignee: TS03 Inc., Quebec (CA)

( * ) Notice: Subject to any disclaimer, the term of this patent is extended or adjusted under 35 U.S.C. 154(b) by 54 days.

(21) Appl. No.: 14/916,622

(22) PCT Filed: Sep. 5, 2014

(86) PCT No.: PCT/CA2014/050845
§ 371 (c)(1),
(2) Date: Mar. 4, 2016

(87) PCT Pub. No.: WO2015/031999
PCT Pub. Date: Mar. 12, 2015

(65) Prior Publication Data
US 2016/0193375 A1 Jul. 7, 2016

Related U.S. Application Data

(60) Provisional application No. 61/874,603, filed on Sep. 6, 2013.

(51) Int. Cl.
A61L 2/24 (2006.01)
A61L 2/20 (2006.01)

(52) U.S. Cl.
CPC ............ A61L 2/24 (2013.01); A61L 2/20 (2013.01); A61L 2/208 (2013.01); A61L 2202/14 (2013.01); A61L 2202/24 (2013.01)

(58) Field of Classification Search
CPC .......................................... A61L 2/24
(Continued)

(56) References Cited

U.S. PATENT DOCUMENTS 4,203,943 A   5/1980  Gillis et al.
4,744,951 A   5/1988  Cummings et al.
(Continued)

FOREIGN PATENT DOCUMENTS

CA   2299914   9/2000
CA   2376117   12/2000
(Continued)

OTHER PUBLICATIONS

Australian Patent Application No. 2014317768, Examination Report dated May 26, 2017.
(Continued)

Primary Examiner — Sean E Conley
Assistant Examiner — Holly M Mull
(74) Attorney, Agent, or Firm — Borden Ladner Gervais, LLP

(57) ABSTRACT

A method for control of a process for sterilizing a load in a sterilization chamber according to specific characteristics of the load without direct measurement of the load conditions. The method preferably includes admitting sterilant gas into the sterilization chamber under vacuum; during admission of the sterilant gas, monitoring a sterilant condensation related parameter or data in the sterilization chamber; detecting the occurrence of condensation and determining a value of the condensation related parameter while detecting condensation; selecting a sterilization cycle among a plurality of predetermined sterilization cycles according to the condensation related data; and performing the selected sterilization cycle for sterilizing the load. The condensation related data may be the sterilant dew point, a degree of condensation, or an amount of condensation which may be determined in monitoring the chamber pressure during sterilant gas admission. The sterilization process may be controlled dynamically according to the determined condensation related data.

17 Claims, 12 Drawing Sheets

(58) Field of Classification Search
USPC .......................................................... 422/33
See application file for complete search history.

(56) References Cited

U.S. PATENT DOCUMENTS

| | | | |
|---|---|---|---|
| 4,956,145 A | 9/1990 | Cummings et al. | |
| 5,527,508 A | 6/1996 | Childers et al. | |
| 5,804,139 A | 9/1998 | Lin et al. | |
| 5,851,458 A | 12/1998 | De Vos et al. | |
| 5,955,025 A | 9/1999 | Barrett | |
| 5,961,922 A | 10/1999 | Witte et al. | |
| 6,106,772 A | 8/2000 | Kohler et al. | |
| 6,218,189 B1 | 4/2001 | Antonoplos et al. | |
| 6,325,972 B1 | 12/2001 | Jacobs et al. | |
| 6,333,002 B1 | 12/2001 | Jacobs et al. | |
| 6,451,254 B1 | 9/2002 | Wang et al. | |
| 6,656,426 B1 | 12/2003 | Wang et al. | |
| 6,852,279 B2 | 2/2005 | Williams et al. | |
| 7,161,677 B2 | 1/2007 | Kawasaki | |
| 7,201,869 B2 | 4/2007 | Williams et al. | |
| 7,670,550 B2 | 3/2010 | Lin et al. | |
| 7,807,100 B2 | 10/2010 | Choperena et al. | |
| 2006/0185189 A1* | 8/2006 | Kawasaki | A61L 2/208 34/468 |
| 2007/0269339 A1* | 11/2007 | Frost | A61L 2/14 422/33 |
| 2009/0060781 A1* | 3/2009 | Adams | A61L 2/208 422/29 |
| 2011/0076192 A1 | 3/2011 | Robitaille et al. | |
| 2013/0243649 A1 | 9/2013 | Dufresne et al. | |
| 2015/0313250 A1* | 11/2015 | Itarashiki | A23L 3/015 426/231 |

FOREIGN PATENT DOCUMENTS

| | | |
|---|---|---|
| CA | 2528333 | 1/2005 |
| EP | 1378248 | 1/2004 |
| GB | 2388545 A | 11/2003 |
| WO | 0121223 A1 | 3/2001 |
| WO | 0170282 A1 | 9/2001 |
| WO | 2004054883 A1 | 7/2004 |
| WO | 2007012866 A1 | 2/2007 |

OTHER PUBLICATIONS

International Patent Application No. PCT/CA2014/050845, International Search Report and Written Opinion dated Nov. 25, 2014.
International Patent Application No. PCT/CA2014/050845, International Preliminary Report on Patentability dated Mar. 17, 2016.
European Patent Application No. 14842982.2, Extended European Search Report dated Jun. 6, 2017.
Chinese Patent Application No. CN201480055976.7, Office Action dated Apr. 4, 2018—English Translation not Available.

* cited by examiner

| Subassembly | |
|---|---|
| Sterilization Chamber (10) | |
| DL-11 | Electro-mechanic Door Lock |
| HTR-11 | Door Flexible Heater (240V / 150W) |
| HTR-12 | Top Chamber Flexible Heaters (240V / 3X-150W) |
| HTR-13 | Bottom Chamber Flexible Heaters (240V / 3X-150W) |
| HTR-14 | Back Chamber Flexible Heater (240V / 150W) |
| PT-11 | Chamber Pressure Transducer non heated type |
| PT-12 | PM Chamber Pressure Transducer non heated type |
| S-11 | Door Closed Switch (Integrated to DL-01) |
| S-12 | Door Lock Switch (Integrated to DL-01) |
| TS-11 | Door Thermal Switch |
| TS-12 | Top Chamber Thermal Switch |
| TS-13 | Bottom Chamber Thermal Switch |
| TS-05 | Back Chamber Thermal Switch |
| TC-11 | Door Thermocouple |
| TC-12 | Top Chamber Thermocouple |
| TC-13 | Bottom Chamber Thermocouple |
| TC-14 | Back Chamber Thermocouple |
| TC-15 | PM Door Thermocouple |
| TC-16 | PM Top Chamber Thermocouple |
| TC-17 | PM Bottom Chamber Thermocouple |
| TC-18 | PM Back Chamber Thermocouple |
| Catalytic Converter (40) | |
| CAT-41 | Catalytic Converter |
| FTR-41 | Catalytic Converter Filter (noise reducer) |
| Vacuum Circuit (50) | |
| FTR-51 | Air Filter for Carulite® Drying Valve |
| M-51 | Dry Vacuum Pump |
| SV-51 | Vacuum Valve, 2/2 way NC pneumatic type |
| SV-52 | Carulite® Drying Valve, 2/2 way NC pneumatic type |
| Electrical Distribution (80) | |
| MC-81 (01) | Micropump Controler Card |
| PLC-81 (01) | Programmable Logical Controler |
| TS-81 (01) | Electrical Panel Thermal Switch |
| VR-81 (01) | Power Supply 240v ac to 120v dc |
| Oxygen /Air Circuit (150) | |
| FTR-151 | Ambient Air Nema Filter |
| SV-151 | Venting Valve, 2/2 way NC pneumatic type (Drive SV-137) |

FIG. 4A

| Subassembly | |
|---|---|
| Compressed Air Circuit (160) | |
| AC-161 | Air compressor |
| AT-161 | Compressed air tank (Integrated to AC-161) |
| DD-161 | Digital Display |
| FTR-161 | Air inlet filter (Integrated to AC-161) |
| PI-161 | Air Pressure indicator (Integrated to AC-161) |
| PR-161 | Printer |
| PS-161 | Pressure switch for air compressor (Integrated to AC-161) |
| RG-161 | Air pressure regulator (Integrated to AC-161) |
| $H_2O_2$ Solution Supply System (130) | |
| B-131 | Custom taper shape bottom $H_2O_2$ Solution bottle |
| BS-131 | Barcode scanner for bottle |
| FC-131 | Flow control for PA-131 (limits actuator puncture speed) |
| FC-132 | Flow control for PA-132 (limits actuator unlocking speed) |
| FC-133 | Flow control for PA-131 (limits actuator upward speed) |
| FTR-131 | Ambient Air Supply, muffler type |
| MV-131 | Manual spill proof valve |
| PA-131 | Pneumatic actuator for bottle puncture |
| PA-132 | Pneumatic actuator for $H_2O_2$ Solution compartment lock |
| S-131 | Sensor (Detects Needle Up position) |
| S-132 | Sensor (Detects Needle Down position) |
| S-133 | Sensor (detects $H_2O_2$ Solution compartment open-close status) |
| S-134 | Sensor (detects the lower level of $H_2O_2$ in the bottle) |
| SV-131 | Micro pump inlet valve, 2/2 way NC solenoid 24 VDC type |
| SV-132 | Micro pump outlet valve, 2/2 way NC solenoid 24 VDC type |
| SV-133 | $H_2O_2$ Filling valve, 3/2 ways NC solenoid 24 VDC type |
| SV-136 | Air pilot valve for needle puncture and compartment locked-unlocked actuators (24VDC – Double Solenoid) |
| SV-137 | Air pilot valve for Venting valve SV-151 (24VDC –Single Solenoid) |
| SV-138 | Air pilot valve for Vacuum valve SV-51 (24VDC –Single Solenoid) |
| SV-139 | Air pilot valve for Drying valve SV-52 (24VDC –Single Solenoid) |
| TA-131 | $H_2O_2$ Storage Tank |
| Vaporization Block (130) | |
| HTR-131 | Vaporization Block Input Heating Element (240V / 125W) |
| HTR-132 | Vaporization Block Output Heating Element (240V / 125W) |
| TC-131 | Vaporization Block thermocouple IN for HTR-131 control |
| TC-132 | Vaporization Block thermocouple OUT for HTR-132 control |
| TC-133 | PM Vaporization Block thermocouple IN for HTR-131 ctrol |
| YC-134 | PM Vaporization Block thermocouple OUT for HTR-132 ctrol |
| TS-131 | Thermal Fuse |

FIG. 4B

STERILIZATION METHODS AND APPARATUS AND ADAPTIVE CONTROL THEREOF

CROSS-REFERENCE TO RELATED APPLICATIONS

This application is a U.S. National Entry of PCT Patent Application No. PCT/CA2014/050845, filed Sep. 5, 2014, which claims the benefit of priority of U.S. Patent Application Ser. No. 61/874,603, filed Sep. 6, 2013, the contents of which are incorporated herein by reference in their entirety.

FIELD OF THE INVENTION

The present invention generally relates to sterilization methods and apparatus and more precisely pertains to a sterilization process using gaseous or vaporized liquid biocides under vacuum.

BACKGROUND OF THE INVENTION

Sterilization is the destruction of any virus, bacteria, fungus or other micro-organism, whether in a vegetative or in a dormant spore state.

Conventional sterile processing procedures for medical instruments involve high temperature (such as steam and dry heat units) or chemicals (such as ethylene oxide gas, hydrogen peroxide or ozone).

Some complex medical devices, such as flexible endoscopes, do not accept high temperature and can therefore not be sterilized with a high temperature technique.

Sterilization methods and apparatus using gaseous chemical sterilants are well known. Sterilizers using hydrogen peroxide as the chemical sterilant are widely used. The hydrogen peroxide is generally supplied as an aqueous hydrogen peroxide solution. This solution is normally evaporated prior to injection into a sterilization chamber of the sterilizer. Evaporation is achieved by heating of the hydrogen peroxide solution, by subjecting the solution in the sterilization chamber or in a separate evaporator to a sufficient vacuum to evaporate the solution, for example by applying a vacuum to the sterilization chamber, or any combination thereof. After evaporation of the hydrogen peroxide solution, the atmosphere in the sterilization chamber includes water vapor and hydrogen peroxide gas. It is a disadvantage of such processes that the water vapor tends to condense on articles upon evaporation of the hydrogen peroxide solution into the chamber, with the resulting layer of condensed water on the articles to be sterilized interfering with the sterilizing action of the hydrogen peroxide gas. Numerous apparatus and process modifications have been developed to address this problem, all of which are aimed at limiting the relative humidity in the sterilization atmosphere during evaporation of the hydrogen peroxide solution and/or during the sterilization process. However, these modifications invariably increase operating cost, sterilization complexity and/or sterilization cycle times. Moreover, hydrogen peroxide solution based processes may still be unsatisfactory regarding the sterilization of specific complex articles with long lumens.

Many hydrogen peroxide sterilizers include a plasma generator in the sterilization chamber to minimize residual hydrogen peroxide that could remain on the sterilized articles, while helping to improve the sterilization process. Although such a technique seems to efficiently minimize residual hydrogen peroxide, it further increases the complexity and manufacturing cost of the sterilizers.

Sterilization processes using both a hydrogen peroxide solution and ozone gas have been developed for the sterilization of complex articles with long lumens. International patent application WO2011/038487, which is incorporated herein by reference, discloses a method for sterilizing an article by sequentially exposing the article to hydrogen peroxide and ozone. Although ozone based processes are satisfactory with respect to the sterilization of complex articles with long lumens, such as flexible endoscopes, material compatibility may still remain a challenge for specific medical devices.

Sterilization processes based on evaporating a hydrogen peroxide solution are generally sensitive to ambient conditions such as ambient temperature and relative humidity and therefore require to be operated in a specific limited range. The articles to be sterilized also have to be in predefined conditions before being sterilized. In some cases, the sterilizer is provided with a separate conditioning chamber particularly devised to adequately condition the load, i.e. conditioning the whole load to a specific temperature and relative humidity, before it is placed in the sterilization chamber. The added conditioning steps and chamber increase sterilization cycle times as well as sterilization cost and may not be very convenient for the operators. Moreover, the requirement for an additional chamber does not allow for a compact design of the sterilizer.

Various conventional hydrogen peroxide sterilizers use sterilant capsules of fixed volume, whereby the content of each capsule is evaporated and injected in a single step. However, due to the differences in vapor pressure and boiling point between water and hydrogen peroxide, this approach leads to disadvantageous effects when the sterilant used is an aqueous hydrogen peroxide solution. Upon sufficient heating, a hydrogen peroxide solution evaporates into water vapor and hydrogen peroxide gas. However, as the temperature of the solution increases, water tends to evaporate first due to its lower boiling point. Thus, upon evaporation of a large amount of water into a sterilization chamber, the initial supply of gas is generally water vapor. This water vapor may condensate on a load in the chamber due to temperature differences between the chamber atmosphere and the load. The resulting layer of condensed water is disadvantageous, since it blocks the hydrogen peroxide gas from reaching the load. Sterilization at the location covered by the water layer is only possible by dissolution of the hydrogen peroxide gas in the water layer, which requires longer cycle times and is disadvantageous, since the concentration of the resulting hydrogen peroxide solution at the covered location is always at most as high as the solution originally evaporated. To address this issue, processes have been developed to increase the concentration of the water vapor/hydrogen peroxide gas mixture during evaporation. However, although this approach increases the concentration of hydrogen peroxide within the layer of condensation on the load, the underlying problem of initially injecting exclusively water vapor during evaporation is not addressed.

More recently, in an attempt to provide more versatile sterilization procedures adapted to different types of loads, hydrogen peroxide sterilization apparatus and processes have been proposed, which include different cycle types for different types of loads. However, those cycles are adapted only to the type of load, and do not take into consideration load conditions such a temperature, humidity, volume and surface area of the load, since standard conditions of load temperature and humidity are assumed for each cycle type.

Thus a selection of predefined sterilization cycles is provided to the operator, which are adapted to certain types of instruments to be sterilized. The operator of the sterilizer is then expected to correctly identify the type of load to be sterilized and select the cycle most appropriate for the load identified. Although this is a step towards more versatility in sterilization treatments, this approach requires the user to be sufficiently sophisticated to not only correctly identify the type of load, but also correctly select the most appropriate cycle from the predefined selection of cycles. This makes these sterilization processes and apparatus more difficult to use and requires the use of trained personnel.

It would therefore be desirable to provide a sterilization method and apparatus that would reduce at least one of the above mentioned drawbacks of known sterilization processes using gaseous or vaporized liquid sterilants.

SUMMARY

It is an object of the present invention to obviate or mitigate at least one disadvantage of previous sterilization processes using sterilant gas from evaporated liquid sterilants.

The inventors have now discovered a manner of controlling a sterilization cycle on the basis of actual load conditions. The inventors have discovered a method of controlling the sterilization taking into control the initial load conditions and preferably also the load conditions occurring during sterilization, most preferably by taking into consideration changes in the load conditions due interaction with the sterilant. Moreover, the inventors have discovered a method of indirectly detecting the load conditions by monitoring sterilant condensation related data or parameters during sterilant injection.

In a first aspect, the invention provides a method for control of a sterilization process according to characteristics of the load to improve sterilant usage and/or efficacy.

In one embodiment of the first aspect, there is provided a method for sterilizing a load in a sterilization chamber comprising the steps of admitting sterilant gas into the sterilization chamber under vacuum; during admission of the sterilant gas monitoring a parameter related to sterilant condensation in the sterilization chamber; upon the occurrence of condensation, determining a value of the condensation related parameter: and selecting a sterilization cycle among a plurality of predetermined sterilization cycles according to the value of the condensation related parameter; and performing the selected sterilization cycle.

The sterilant condensation related data are dependent on the conditions of the load, such as load size, composition and temperature. Thus, by monitoring the sterilant condensation related parameter, optimization of the sterilization process, i.e. the sterilization cycle parameters, according to the specific conditions of the load is made possible without direct measurement of the load conditions.

In one embodiment, the step of monitoring the sterilant condensation related parameter includes monitoring an actual pressure of the sterilization chamber atmosphere during admission of the sterilant gas and comparing the actual pressure to a theoretical vapor pressure of the sterilant for detecting a deviation between the actual pressure and the theoretical vapor pressure.

In another embodiment, the step of monitoring the sterilant condensation related parameter comprises a determination of the sterilant dew point inside the sterilization chamber, i.e. the moment at which condensation commences.

In a further embodiment, the sterilant condensation related parameter monitored is a rate of pressure increase inside the chamber during admission of the sterilant gas at a constant rate and the sterilant dew point is determined by detecting a change in the rate of pressure increase.

In still a further embodiment, the liquid sterilant is an aqueous hydrogen peroxide solution, which is evaporated to generate the sterilant gas, hydrogen peroxide gas. Successive pulses of hydrogen peroxide solution are evaporated into water vapor and hydrogen peroxide gas prior to admission into the sterilization chamber in such a way that the hydrogen peroxide gas and water vapor of each pulse are simultaneously admitted into the sterilization chamber.

In yet a further embodiment, the admission of sterilant gas into the sterilization chamber comprises completely evaporating successive pulses of hydrogen peroxide solution, each solution pulse being evaporated into a mixture of water vapor and hydrogen peroxide gas prior to injection of the mixture pulse into the sterilization chamber. In this manner it is assured that all of the water vapor and hydrogen peroxide gas originating from each pulse is simultaneously admitted into the chamber.

In another embodiment of the first aspect, there is also provided a method for sterilizing a load in a sterilization chamber under vacuum, comprising admitting a sterilant gas into the sterilization chamber under vacuum; during admission of the sterilant gas monitoring a parameter related to sterilant condensation in the sterilization chamber; detecting the onset of condensation in the chamber and determining a value of the condensation related parameter at the onset of condensation; selecting a sterilization cycle among a plurality of predetermined sterilization cycles according to the value of the condensation related parameter; and performing the selected sterilization cycle for sterilizing the load.

In a second aspect, there is provided a method for dynamically controlling a sterilization process, the method comprising placing a load to be sterilized into a sterilization chamber under vacuum; admitting sterilant gas into the sterilization chamber; monitoring sterilant condensation related data in the sterilization chamber during sterilant gas admission; and controlling the sterilization process according to the data detected.

In an embodiment of the second aspect, the sterilization process is controlled by controlling one or more sterilization cycle parameters. These sterilization cycle parameters may be volume of injected sterilant, rate of sterilant injection, sterilant injection end pressure, volume of compression gas injected, rate of compression gas injection, dwell time characteristics, sterilant evacuation parameters and number of ventilations to perform, as non-imitative examples.

By monitoring the effect of the specific load conditions on the sterilant condensation behavior, the sterilization process can be tailored to accommodate a wide range of specific load conditions, including a wide range of load temperatures, which is of great advantage.

In a third aspect, the invention provides a method for dynamic admission of sterilant into a sterilization chamber.

In one embodiment of the third aspect, there is provided a method for dynamic admission of sterilant into a sterilization chamber under vacuum, the method comprising admitting sterilant gas into the sterilization chamber under vacuum; measuring sterilant condensation related data in the sterilization chamber during sterilant admission; determining at least one selected admission parameter according to the measured condensation related data; and completing sterilant admission according to the at least one selected admission parameter.

In one embodiment of the third aspect, the selected admission parameter may be the total volume of admitted sterilant. In another embodiment, it may be the sterilant admission end pressure.

The step of measuring the condensation related data may comprise detection of the sterilant dew point inside the sterilization chamber.

In a fourth aspect, the invention provides a method for determining a sterilant dew point in a sterilization chamber according to existing load conditions, the method comprising admitting sterilant gas into the sterilization chamber under vacuum; monitoring a rate of pressure increase inside the chamber during sterilant admission; detecting a change in the rate of pressure increase; and determining the dew point according to the detected rate change.

The method of the invention allows for the indirect determination of load conditions in the sterilization chamber without measuring of the load conditions, which is of great advantage. Thus, the method may further be used to tailor a sterilization process according to the indirectly determined load conditions.

In a fifth aspect, the invention provides a method for determining load conditions of a load placed in a sterilization chamber, the method comprising detecting a sterilant dew point in the sterilization chamber during sterilant admission; and determining the load conditions according to the detected dew point.

In a sixth aspect, the invention provides an apparatus for sterilizing a load, including a sterilization chamber, a vacuum arrangement for applying a vacuum in the sterilization chamber, a sterilant injection arrangement for admitting a sterilant gas into the sterilization chamber when under vacuum; a monitoring arrangement for monitoring a sterilant condensation related parameter in the sterilization chamber during admission of the sterilant gas and for determining a value of the condensation related parameter upon the occurrence of condensation in the chamber; and a control unit connected to the monitoring unit for selecting a sterilization cycle among a plurality of predetermined sterilization cycles according to the value of the condensation related parameter detected by the monitoring unit. Preferably, the injection arrangement is constructed for admitting the sterilant gas at a constant rate.

Preferably, the sterilant condensation related parameter monitored by the monitoring arrangement is dependent on a condition of the load when placed in the chamber.

In a preferred embodiment of the sixth aspect, the sterilant injection arrangement provides the sterilant gas at a constant rate and the sterilant condensation related parameter monitored by the monitoring arrangement is the chamber pressure. Preferably, the monitoring arrangement monitors the pressure in the sterilization chamber for at least one of a change in a rate of pressure increase in the sterilization chamber during admission of the sterilant gas, a deviation of a monitored chamber pressure curve from a theoretical chamber pressure curve, a degree of deviation of the monitored chamber pressure curve from the theoretical chamber pressure curve and an amount of the deviation of the monitored chamber pressure curve from the theoretical chamber pressure curve at two or more points in time, for detecting the occurrence, onset or degree of condensation in the chamber.

In another preferred embodiment of the sixth aspect, the control unit is adapted to select the sterilization cycle based on a degree of condensation detected by the monitoring arrangement, the pressure in the chamber at the onset of condensation, or a curve of the pressure in the chamber during the occurrence of condensation. Preferably, the control unit is adapted to select the sterilization cycle based on the pressure in the chamber at the point in time where the change in the rate of pressure increase is detected by the monitoring arrangement.

In a further preferred embodiment of the sixth aspect, the monitoring unit determines from an area between the monitored chamber pressure curve and the theoretical chamber pressure curve a quantity of condensed sterilant gas and the control unit selects the sterilization cycle on the basis of the amount of condensed sterilant gas.

In yet another preferred embodiment of the sixth aspect, the monitoring unit determines from an area between the monitored chamber pressure curve and the theoretical chamber pressure curve a quantity of condensed sterilant gas and the control unit selects the sterilization cycle on the basis of a ratio of the amount of condensed sterilant gas determined by the monitoring unit and a total amount of injected sterilant gas determined by the injection arrangement. Preferably, the control unit selects the sterilization cycle on the basis of a remaining quantity of sterilant gas to inject. Alternatively, the control unit can select the sterilization cycle based on a desired chamber pressure at the end of sterilant gas admission.

BRIEF DESCRIPTION OF THE DRAWINGS

In order that the invention may be readily understood, embodiments of the invention are illustrated by way of example in the accompanying drawings.

FIG. 4A and FIG. 4B are tables listing the parts of the sterilization apparatus shown in FIG. 1 to FIG. 3;

Figure 1:
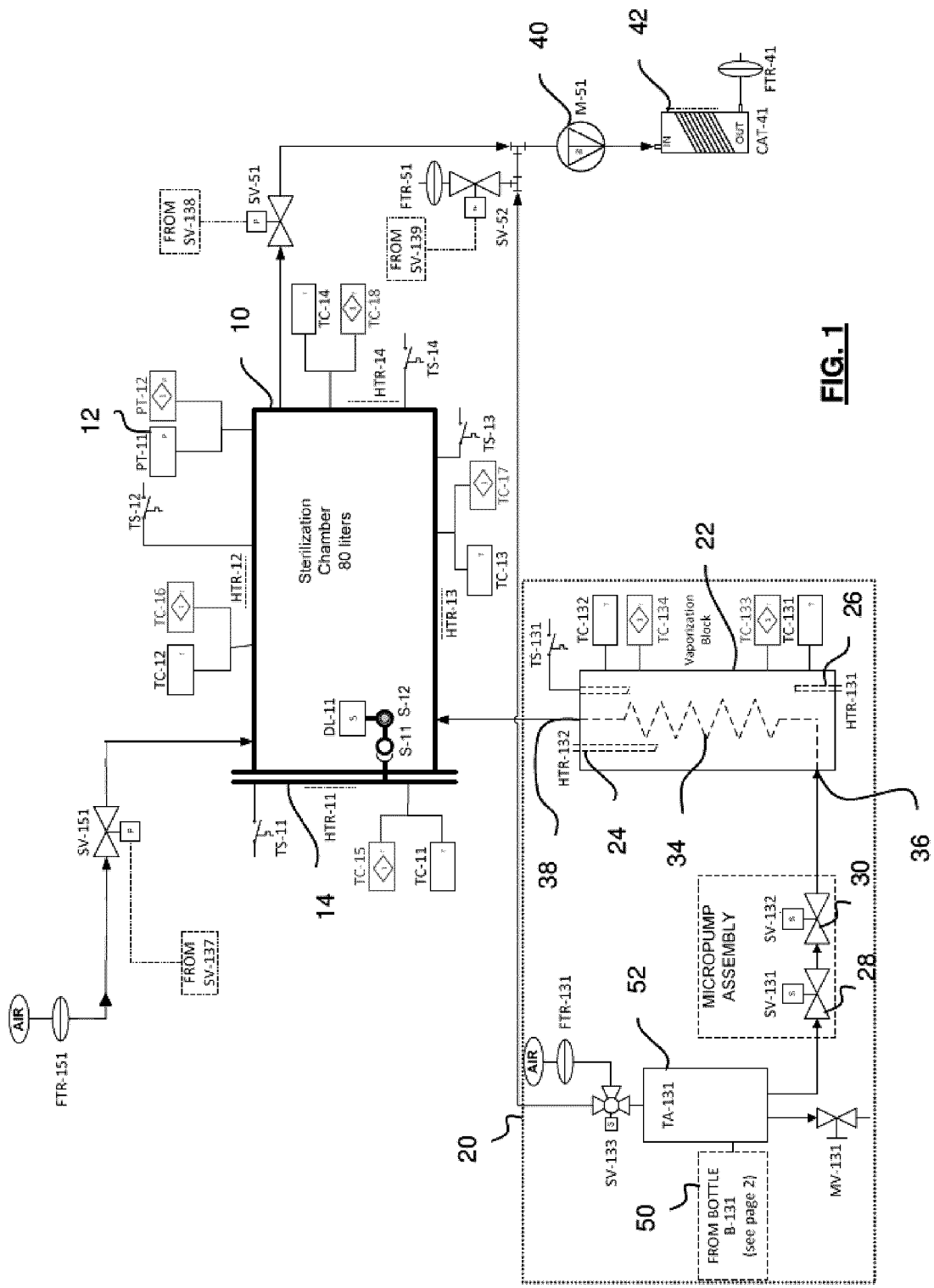
FIG. 1 is a schematic diagram of a sterilization apparatus, according to one embodiment of the invention, the illustrated parts of the apparatus being listed in the tables of FIG. 4A and FIG. 4B.

Further details of the invention and its advantages will be apparent from the detailed description included below.

DETAILED DESCRIPTION

In the following description of the exemplary embodiments, references to the accompanying drawings are by way of illustration of examples by which the invention may be practiced. It will be understood that other embodiments may be made without departing from the scope of the invention disclosed.

The term "sterilization" generally refers to rendering a substance incapable of reproduction, metabolism and/or growth. While this is often taken to mean total absence of living organisms, the term may be used herein to also refer to a substance free from living organisms to a target degree previously agreed to be acceptable. Thus, unless otherwise indicated, the term sterilization may be used herein to also refer to methods and procedures less rigorous than sterilization, for example, decontamination and the like. Moreover, although the methods of the invention will be described herein in the particular field of sterilization of medical devices, the skilled addressee will appreciate that other applications may be envisaged, for example various commercial and industrial applications.

In this specification, the term sterilization chamber under vacuum refers to a previously evacuated chamber which has been sealed except for admission of the sterilant.

This specification is related to sterilization processes using liquid sterilants which during a sterilization cycle are evaporated to generate sterilant gas. Thus, any reference to sterilant gas throughout this specification refers to an evaporated liquid sterilant. Where the sterilant used is in the form of an aqueous solution, the term sterilant gas refers to the evaporated sterilant component of the solution.

In this specification, the terms condensation related parameter and condensation related data refer to parameters and data reflective of sterilant condensation and may be indicative of an absence of sterilant condensation, an onset of sterilant condensation, or a progression of sterilant condensation.

The term control of the sterilization process as used herein refers to the control of one or more sterilization cycle parameters, selected from the group of the volume of injected sterilant (a measured actual volume, or relative volume determined on the basis of the number of injection pulses, the overall injection time, or a sterilant admission end pressure inside the chamber), the rate of sterilant injection, the injected compression gas quantity, the rate of compression gas injection, various dwell time parameters (pressure level and length), various sterilant evacuation parameters (rate or duration) and number and/or parameters of ventilations to perform. Non-limitative examples of sterilization control will be described further below.

Throughout the present description, the invention will be described in relation to one particular exemplary embodiment wherein the biocide used for sterilization is hydrogen peroxide. In the preferred embodiment, an aqueous solution of hydrogen peroxide, preferably a 50 wt % hydrogen peroxide solution, typically provided with additives and/or stabilizers, such as the STERIZONE® 125-280 Solution™ from TSO₃ Inc, is used to generate the sterilant gas. The skilled addressee will appreciate that other concentrations of the solution (3% to 59% for non-limitative examples) or other liquid biocides for evaporation may be envisaged for a specific application without departing from the scope of the invention.

The present invention generally relates to sterilization methods wherein a liquid sterilant, preferably hydrogen peroxide, is first evaporated to generate sterilant gas, preferably hydrogen peroxide gas. The sterilant gas is then admitted into an evacuated sterilization chamber and then condensed into a microlayer of sterilant on the load in the chamber as the chamber pressure gradually increases due to admission of the evaporated sterilant. After sterilant condensation, evacuation of the atmosphere inside the chamber, sometimes a controlled evacuation, is then performed to achieve a targeted sterility or decontamination assurance level of the article, as it will become apparent below. As is well known to the skilled addressee, such operation, which may be called a half cycle, may be repeated a subsequent time for regulatory purposes to meet a sterility assurance level of $10^{-6}$ or a 12-log reduction requirement for a complete sterilization). Once the process cycle is completed, the chamber is then ventilated for removing residual hydrogen peroxide that may remain in the chamber and/or on the articles. As described thereinafter, the chamber may be alternatively exhausted and aerated with appropriate gas such as fresh air for a non-limitative example to ensure an efficient removal of the sterilant before releasing the sterilized article.

The sterilization methods of the invention are preferably carried out at room temperature and, thus, require substantially no cooling down of sterilized articles so that they can be used immediately following the sterilization cycle, which is of great advantage. This allows hospitals to reduce the cost of maintaining expensive medical device inventories. The sterilization method of the invention offers several further advantages. It minimizes toxic waste, does not require the handling of dangerous gas cylinders, and minimizes the threat to the environment or the user's health. Stainless-steel instruments and heat-sensitive instruments can be treated simultaneously, which for some users will obviate the need for two or more different types of sterilizers. Moreover, the sterilizer may have a compact design, which is of great advantage for use directly in an operating room.

As will become apparent to the skilled addressee upon reading of the present description, according to one aspect, the invention relates to sterilization methods implementing an adaptive control of at least one sterilization process parameter in order to provide a tailored sterilization cycle specifically adapted to the load to be sterilized. Such a method is of great advantage since it enables to ensure an adequate sterilization of the load with appropriate exposure to sterilant while being adapted to provide an optimized sterilization process, for example with an improved material compatibility and/or a reduced processing time, as it will be described below.

In one embodiment, the invention provides a method for sterilizing a load in a sterilization chamber wherein sterilant gas is admitted into the sterilization chamber under vacuum, which preferably is a previously evacuated chamber that has been sealed except for admission of the sterilant. As will be discussed in detail below, sterilant condensation related data are measured in the sterilization chamber during admission of the sterilant gas. A sterilization cycle is then selected among a plurality of predetermined sterilization cycles according to the measured condensation related data. The sterilant condensation data may be a variation between a theoretical pressure curve expected during admission of the sterilant gas and an actually measured pressure curve, or data related thereto, such as an area between both curves, an area between tangents to the expected and actual curves, or data related to the onset of condensation, such as a change in slope of the expected curve, or data indicating the actual sterilant dew point inside the sterilization chamber. The selected sterilization cycle is then performed for sterilizing the load.

Indeed, while optimizing various sterilization processes in a sterilization chamber, tests have shown that sterilization results greatly depend on the specific conditions of the load, including its composition, size and temperature. Load size in this context refers to the number and size of medical instruments loaded into the chamber. Although conditioning of the load is possible to render the sterilization outcome more reliable, the conditioning is not always reliable and not only makes the sterilization process more difficult and involved, but also extends sterilization cycle times. Thus, controlling the sterilization process according to the actually occurring load conditions, without pre-conditioning of the load, will render sterilization process more reliable and controllable while avoiding excess sterilant usage and minimizing cycle times.

In analyzing the occurrence of condensation, the onset of condensation, or the dew point, inside the chamber during sterilant gas admission, with respect to the reliability of the respectively achieved sterilization, the inventors have found that sterilant condensation related data are directly related to and the most reliable indicator of the actual conditions of the Load. For example, the inventors have found that the behavior of the chamber pressure upon admission of the sterilant gas at a constant rate is directly related to the load conditions. Thus, the shape and slope of the pressure curve on its own and in comparison to a theroretically expected pressure curve with no load present in the chamber is indicative of the load conditions. Moreover, the pressure level at the onset of condensation (the dew point), i.e. the moment when condensation begins, is directly related to the specific conditions of the load. Changes in the chamber pressure curve which deviate from the changes expected on the basis of the theoretical vapor pressure curve of the sterilant gas are also indicative of the specific conditions of the load and can be used for the selection of a cycle appropriate to achieve sterilization at the load conditions associated with the measured parameters.

In view of those surprising findings, the inventors have developed the method of the present invention for adaptive control of sterilization processes using condensation related data detection for identification of a sterilization cycle appropriate for the load conditions generating the condensation related data. Since this method is adaptive to the actual load conditions, it can be used to process in an automatic manner a wide range of loads at a wide range of load conditions, including a wide range of load temperature, without requiring any prior lengthy conditioning of the load, which is of great advantage. Indeed, in one embodiment, loads which temperatures ranged from 16° C. to 37° C. as a non-limitative example could be successfully processed.

In contrast to known sterilization protocols in which the load has to be conditioned to adapt the load conditions to a fixed sterilization cycle, which at best results in an approximation of the load conditions to the cycle parameters, the method of the present invention dynamically adjusts the sterilization cycle to the exact load conditions detected during the actual sterilization process. In other words, the present method can be used to adapt the process cycle to the load conditions, rather than providing fixed cycles to which the load has to be adapted, thereby providing more flexibility of use to the user, which is also of great advantage. The method is also particularly robust and may reduce the number of canceled cycles typically caused by initial conditions out of the operating ranges of known sterilizers.

Adaptation of the sterilization cycle to the load conditions, especially the amount of sterilant gas injected, is important for reliable sterilization, not only with respect to the injection of a sufficient amount of sterilant, but to prevent the injection of an excess amount of sterilant, which may lead to unsatisfactory sterilization results as will be discussed below.

Various conventional hydrogen peroxide sterilizers use sterilant capsules of fixed volume, whereby the whole content of each capsule is evaporated and injected in a single step. However, due to the differences in vapor pressure and boiling point between water and hydrogen peroxide, this approach leads to disadvantageous effects when the sterilant used is an aqueous hydrogen peroxide solution. Upon sufficient heating, a hydrogen peroxide solution evaporates into water vapor and hydrogen peroxide gas. As the temperature of the solution increases, water tends to evaporate first due to its lower boiling point. Thus, upon evaporation of a large amount of water into a sterilization chamber, the initial supply of gas is generally water vapor. This water vapor may condensate on the load in the chamber due to temperature differences between the chamber atmosphere and the load. The resulting layer of condensed water is disadvantageous, since it blocks the hydrogen peroxide gas from reaching the load. Sterilization at the location covered by the water layer may only be possible by dissolution of the hydrogen peroxide gas in the water layer, which requires longer cycle times and is disadvantageous, since the concentration of the resulting hydrogen peroxide solution at the covered location is always at most as high as the solution originally evaporated. To address this issue, processes have been developed to increase the concentration of hydrogen peroxide gas in the water vapor/hydrogen peroxide gas mixture during evaporation. However, although this approach increases the concentration of hydrogen peroxide within the layer of condensation on the load, the underlying problem of initially injecting exclusively water vapor during evaporation is not addressed.

In contrast, in a preferred embodiment of the invention, an aqueous sterilant solution including a sterilant having a boiling point higher than water is evaporated in small solution pulses to create subsequent mixture pulses of a water vapor/sterilant gas mixture that are admitted into the sterilization chamber. In this respect, the volume of each solution pulse is selected such that both the water and the sterilant in the mixture pulse are fully evaporated and in the gaseous state prior to admission of the mixture pulse into the sterilization chamber. This ensures that the water vapor and sterilant gas both arrive at the load substantially at the same time. Due to the higher boiling point of the sterilant and by ensuring a simultaneous arrival of both components of the mixture, the present method not only avoids the possibility of a condensed water microlayer on the load, but ensures the formation of a condensed sterilant microlayer of very low water content on the load. This is particulary true when the sterilant is hydrogen peroxide because of the saturation vapor pressure differential. Thus, in contrast to known hydrogen peroxide sterilization processes in which a water microlayer is formed first, the sterilant content of which gradually increases during the sterilization cycle, in the preferred process of the invention a sterilant microlayer is formed, the water content of which gradually increases during the sterilization cycle. This is achieved by taking advantage of the selective condensation of hydrogen peroxide over water from the admitted mixture of hydrogen peroxide gas and water vapor. Consequently, the microlayer which can form on the load in the present process has a very high initial sterilant concentration that is much higher than the concentration of the starting solution used, whereas the microlayer formed in conventional processes initially has a very low sterilant concentration which gradually increases to at most the concentration of the starting solution. This microlayer of a sterilant concentration much higher than the starting solution contributes to a high sterilization reliability of the present process. For a 50 wt % solution, the condensation commences at a couple of Torr and is about 85%.

Figure 10:
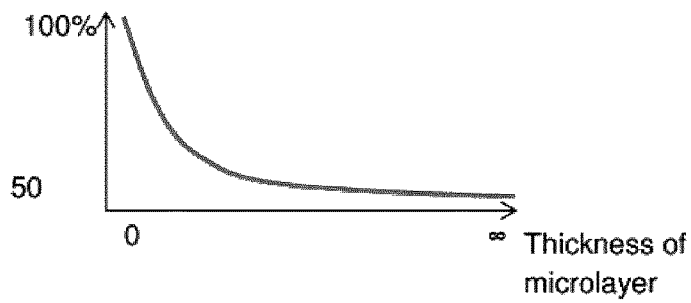
FIG. 10 illustrates the relationship between the thickness of the microlayer and the concentration of the sterilant in the layer.

Controlling the sterilization process to avoid the admission of an excess amount of sterilant gas is desired in order to avoid the formation of a microlayer of excessive thickness, since the inventors have discovered that the sterilant concentration in the microlayer exponentially decreases with an increase in microlayer thickness (see FIG. 10). Thus, to maintain a maximum concentration of the sterilant in the microlayer, the thickness of the microlayer should be kept as small as possible. Consequently, after formation of the microlayer of sterilant gas condensation on the load, it will be advantageous to control the admission of additional sterilant gas to replace the condensed sterilant which has decomposed due to contact with the load, contaminants on the load, or simply due to ongoing decomposition of the sterilant.

In one aspect of the present method for controlling a sterilization process dynamically, a load to be sterilized is placed in a sterilization chamber under vacuum in a first step. In a second step, sterilant gas is stepwise admitted into the sterilization chamber under vacuum, while condensation related data in the sterilization chamber are monitored. The overall sterilization process is controlled according to the condensation related data detected. Different methods for detecting condensation related data will be discussed further below. In one exemplary embodiment, a dew point detection is used.

In one exemplary embodiment of the first aspect, sterilant condensation related data in the sterilization chamber are measured during sterilant gas admission into the sterilization chamber under vacuum, whereby the sterilant gas is admitted into the chamber until at least a predetermined pressure above all dew points expected for any type of load is reached. At least one selected admission parameter is determined according to the measured condensation related data and the sterilant gas admission is completed according to the determined at least one selected admission parameter. The selected admission parameter is preferably the total volume of sterilant gas admitted into the chamber, or the sterilant admission end pressure. In one embodiment, the condensation related data represent the detected pressure level at the dew point inside the sterilization chamber.

As it should be apparent to the skilled addressee, the methods described above rely on the detection of condensation related data inside the sterilization chamber during sterilant gas admission. Different methods for determining condensation related data will be discussed in the following.

I—Dew Point Detection

If the condensation related data reflect the chamber pressure at the onset of condensation on the load the pressure level inside the chamber at the dew point of the sterilant gas is detected during sterilant gas admission. Such dew point will generally depend on the specific characteristics of the load, including its temperature. The detected dew point may then be advantageously used to adapt various predetermined parameters of a selected sterilization cycle to sterilize the specific load therewith, as it should become apparent upon reading of the present description.

Various methods may be used to detect the dew point in the sterilization chamber during sterilant gas admission. For example, dew point sensors and/or UV detection systems may be used. However, in a preferred embodiment, the dew point is determined by monitoring the pressure increase inside the sterilization chamber during sterilant gas admission, as detailed below. In another embodiment, appropriate sensors may be used to monitor other condensation related parameters. For example, the formation of a micro-layer of condensate may be detected, or even the thickness of such a micro-layer.

According to the third aspect of the invention, the invention provides a method for detecting a dew point, i.e. the onset of condensation, in a sterilization chamber depending on the load conditions. In the method, sterilant gas is admitted into the sterilization chamber under vacuum while a rate of pressure increase inside the chamber is being monitored. The sterilant gas is admitted into the chamber until at least a predetermined pressure above all dew points expected for any type of load is reached. Preferably, and as detailed below, the sterilant gas is supplied to the sterilization chamber by evaporation of successive pulses (increments) of hydrogen peroxide solution to generate successive pulses of a water vapor/hydrogen peroxide gas mixture and admission of the mixture into the sterilization chamber at a constant rate, but other sterilant gas admission techniques may also be considered. A change in the rate of pressure increase (indicating the beginning of condensation) is detected to then determine the dew point according to the detected rate change, as will be described in more detail below. This method is of great advantage since it is very simple to implement and does not require expensive or cumbersome equipment, for example for the monitoring of the load conditions.

The dew point is directly related to the temperature of the load. The relative temperature of the load takes into consideration the thermal temperature of the load and the temperature affinity (i.e. the affinity between the type of material, the nature of the materials, their surface finish, geometry . . . ) of the load.

The temperature affinity is much more difficult to quantify, since every material has a different behavior. Certain materials, such as plastics, are very hydrophobic and don't have a natural affinity to products of a nature similar to that of water. Hydrophobic materials therefore have the tendency to delay the moment at which condensation forms, compared to a more hydrophilic material. Moreover, if the surface is very smooth, the formation of the condensation is less present than on very rough surfaces, or porous surfaces. Certain geometries, such as cracks or gaps could favor locally a premature formation of the microlayer. Other materials, such as aluminum have a higher capacity to capture the energy of the thermal temperature and their temperature varies more easily; the warmer the surface during injection, the more the dew point is retarded. The temperature affinity is therefore affected by these factors and others which create variations in the dew point.

During the sterilization cycle the determination of the dew point is used to carry out a sterilization cycle which has a higher sterilization efficacy within its use parameters. The advantage of this method is that it is non-invasive, does not require the direct reading of the temperature and takes into consideration the heating/cooling to which the load can be subjected during initial vacuum or subsequent injection steps (radiation, conduction or evaporation during evacuation steps or at a plateau).

Figure 8:
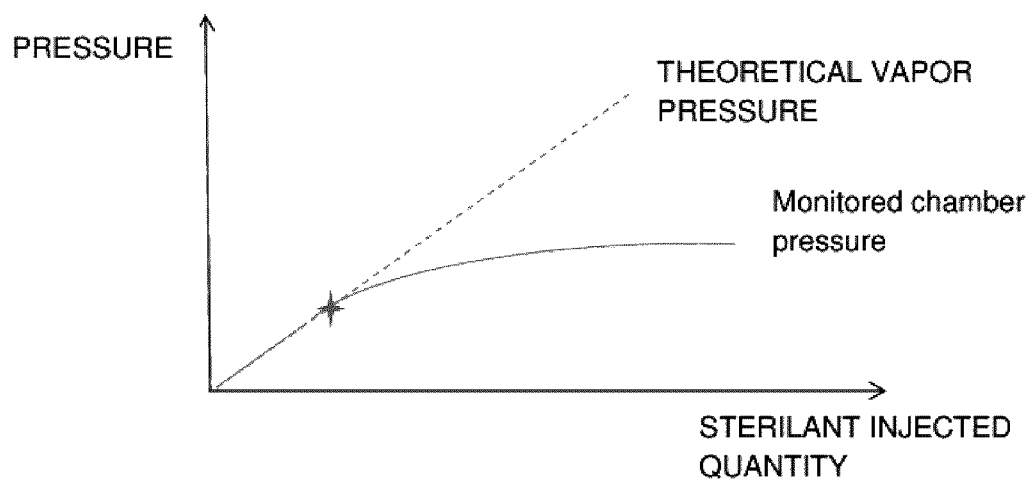
FIG. 8 is an exemplary representation of a pressure profile in a sterilization chamber, used in a first method of determining a condensation related parameter, namely the dew point.
Figure 9:
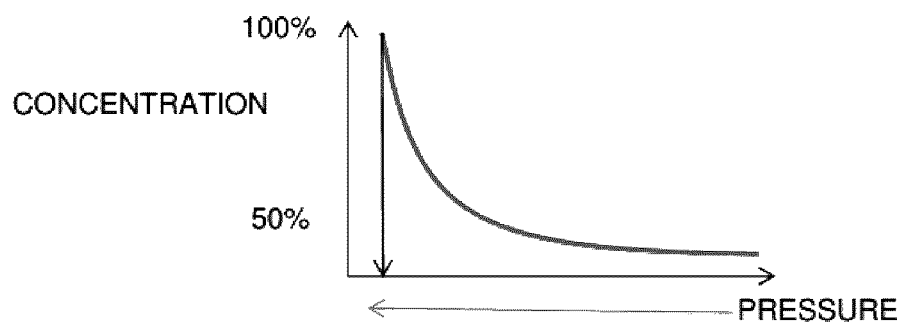
FIG. 9 illustrates the relationship between the chamber pressure and the concentration of the sterilant in the microlayer during sterilant evacuation.

The dew point is determined by finding the point of inflection of the chamber pressure curve, which is the point of departure of the chamber pressure curve from the theoretical vapor pressure curve of the hydrogen peroxide gas injected. This point of inflection is signified by a change in the slope of the chamber pressure curve. At the dew point, the chamber pressure curve changes from a straight line to a curve, as shown in FIG. 8.

Figure 15:
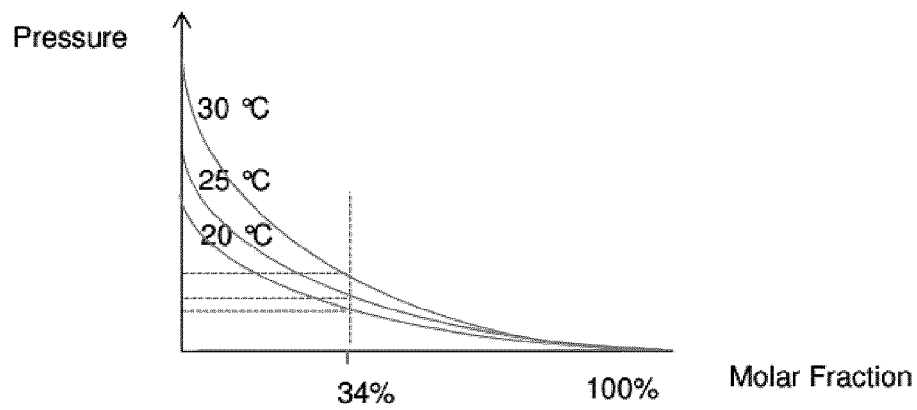
FIG. 15 illustrates the relationship between the molar fraction of a 50 wt % hydrogen peroxide sterilant solution and pressure at different temperatures.

By determining the pressure at which condensation first occurs, i.e. the dew point, one can determine not only the temperature of the load, but also how the injection should be carried out in order to ensure sterility. The relationship between the dew point and the temperature is explained by thermodynamics and by consulting an isothermal curve for a mixture of hydrogen peroxide and water. For example, 50 wt % hydrogen peroxide has a molar fraction of 0.34. By calculating the liquid curve of this mixture at several temperatures it is possible to predict its behavior, as shown in FIG. 15. Once the pressure surpasses the liquid curve for a given temperature and mixture, condensation of vapor commences.

When gaseous hydrogen peroxide is condensed, it is no longer available for pressure buildup in the chamber. Therefore, a break or inflection point appears on the chamber pressure curve. This break, the dew point, then indicates the disruption of the vapor phase equilibrium, caused by the liquid phase and indicates the relative temperature of the load. The liquid condensates on the colder surfaces, which means the load and not the surrounding surfaces of the chamber, to form a microlayer.

Several experimental tests were run at different temperatures with the goal to detect a theoretical dew point for various loads. For an analysis of the table below one must keep in mind that the temperature of the load is a temperature adjusted prior to insertion of the load into the chamber and does not take into account the temperature affinity of the load and the temperature changes within the sterilizer. It is therefore normal to see a slight difference between the detected and theoretic dew point values. Nevertheless, it is noted that the practical values are close to the theoretic values.

TABLE 1

| Dew Point | | | | |
|---|---|---|---|---|
| Temperature (° C.) | Theoretical Dew Point (torr) | Load reference* | Detected Dew Point (Torr) | Injected Quantity of sterilant solution (delta P, Torr) |
| 18 +/− 2 | $3.048_{+0.48}^{-0.42}$ | F | 2.5 | 13-17 |
| | | F | 2.5 | |
| | | R | 3.1 | |
| | | R | 3.1 | |
| | | F | 3.1 | |
| | | R | 3.2 | |
| | | F | 3.3 | |
| | | R | 3.3 | |
| | | F | 3.3 | |
| | | F | 3.4 | |
| 25 +/− 2 | $5.030_{+0.744}^{-0.658}$ | F | 4.6 | 25-29 |
| | | F | 4.6 | |
| | | F | 4.8 | |
| | | F | 4.8 | |
| | | F | 4.9 | |
| | | F | 5.0 | |
| | | R | 5.3 | |

TABLE 1-continued

| Dew Point | | | | |
|---|---|---|---|---|
| Temperature (° C.) | Theoretical Dew Point (torr) | Load reference* | Detected Dew Point (Torr) | Injected Quantity of sterilant solution (delta P, Torr) |
| 30 +/− 2 | $7.071_{+1.002}^{-0.89}$ | F | 5.6 | 30-35 |
| | | F | 5.7 | |
| | | R | 5.7 | |
| | | R | 5.7 | |
| | | R | 5.7 | |
| | | F | 5.7 | |
| | | F | 5.7 | |
| | | R | 5.7 | |
| | | R | 5.7 | |
| | | F | 5.8 | |

*The Load reference identifies the type of load used for each test. Load reference F indicates a load of a first wrapped tray containing a flexible endoscope and a second tray with a camera and a fiber optic cable as well as other stainless steel instruments. Load reference R indicates a first wrapped tray with two doubled-channelled rigid endoscopes; and a second wrapped tray with a camera and fiber optical cable and two small rigid containers with stainless steel devices.

Once the dew point has been detected, it is possible to manage the injection with several different methods in a manner to obtain a microlayer of sufficient thickness for each surface of the load to achieve sterilization but without excessive dilution. As previously mentioned, one can add a fixed pressure increment according to the detected load, as shown in Table 1 above and detailed hereinafter. To do this, one determines the dew point and then add an incremental pressure. Empirical testing has shown that the incremental pressure increase can be proportional to the value of the detected dew point. For example, for a dew point of 6.9 Torr, the injection can be terminated at 30 Torr. The skilled addressee will appreciate that the quantity of injected sterilant is not predetermined, nor fixed and is adapted to each specific load.

In the test series conducted, the results of which are shown in Table 1, the load condition information reflected by the dew point detected was used to adjust the sterilization cycle. In particular, the load condition information was used to adjust the amount of sterilant gas injected. This was done by choosing, on the basis of the dew point value, a fixed additional pressure increment for which sterilant gas admission into the sterilization chamber was continued and after the achievement of which admission was terminated. All tests conducted were successful in achieving sterilization. As can be seen from the results in Table 1, a clear correlation exists between the temperature of the load and the dew point. More importantly, choosing a total amount of sterilant gas directly correlated to the dew point value was successful in achieving satisfactory sterilization. Thus, the test series has shown that controlling the sterilization cycle, in particular the amount of sterilant used, on the basis of the load conditions does not require the detection of the load conditions prior to sterilant injection. Moreover, the test series has shown that satisfactory sterilization can be achieved by controlling the sterilization cycle on the basis of data related to the condensation of sterilant gas in the chamber during sterilization of the load. The test series has also shown that condensation related data, and parameters, for example the sterilant gas dew point in the presence of the load, are a good indicator of the load condition and can be successfully used to control the overall amount of sterilant used.

Alternatively, one can add an incremental time or number of pulses after detection of the dew point to complete the injection. Optionally, the added injection time may be proportional to the injection time required to reach the dew point. In one exemplary embodiment, after the dew point was detected at 5 Torr another 5 min of injection time was added, or another 300 mixture pulses were admitted to complete the injection.

II—Amount of Liquid Condensed

Figure 11:
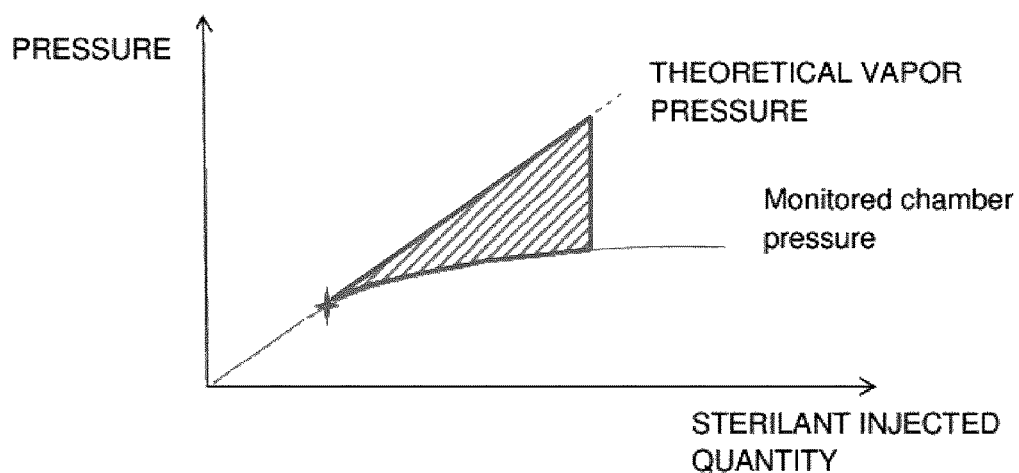
FIG. 11 illustrates a second method of determining a condensation related parameter.

It is possible to determine the liquid condensed by integrating the area of liquid which is no longer present in the gas. The integration of this area can be done mathematically by directly calculating the area between the theoretical vapor pressure line and the actual pressure measured in the chamber as illustrated in FIG. 11. A minimum area is then determined according to empirical testing for ensuring sterility and as soon as that area has been reached, sterilant injection is stopped. For example, a predetermined area of 6000 min·Torr is set for completion of the injection, as detailed below. According to this method, detection of the dew point is not required.

III—Differential Between Curves

Figure 12:
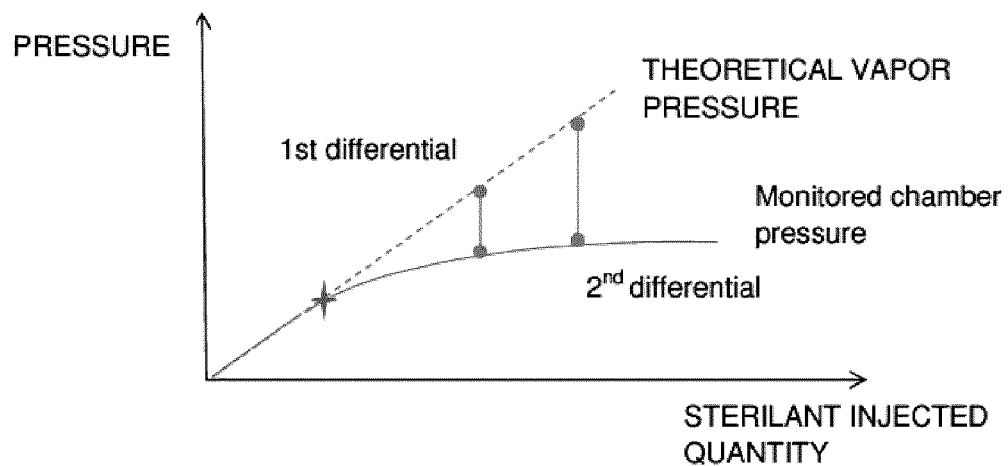
FIG. 12 illustrates a third method of determining a condensation related parameter.

One can also trace one or more of the distances between the theoretical and actual curves as illustrated in FIG. 12. One can then determine for those sections a minimum length needed for sterilization. In one example, a single differential is used. Based on the theoretical pressure curve for 100% vapor and the real pressure curve, one can establish by empirical testing the pressure differential ($\Delta P$) required between the two curves to sterilize the load. This method, same as the previous one, does not rely on the dew point detection since only the difference between the real and theoretical curves is used.

IV—Ratio of Differentials Between Curves

A ratio between the different lengths of the distances between the theoretical and actual curves can also be determined, again as illustrated in FIG. 12. A specific ratio can then be determined which is sufficient to achieve sterilization. For example, one could determine that the length of the second differential should be a factor of 2 larger than the first differential.

V—Area Defined By Differentials Between Curves

It is possible to calculate an area between the curves from the differentials, using the geometry of a trapeze [(short differential+long differential)×time/2] as illustrated in FIG. 12. One can then determine a minimum area required to achieve sterilization and control the sterilization process for sterilant gas admission to stop when the minimum area is reached. This area is in the following referred to as the area above the curve.

To determine whether the area above the actual pressure curve is indicative of the load conditions, a series of tests were conducted with complex loads representing a maximum capacity of the sterilizer apparatus used 80 liters chamber model, TSO3 80 L prototype). The results are represented below in Table 2. The dew point values are included only for comparison with the test series represented by the results in Table 1. The dew point was detected during injection. However, in the present test series the dew point was not used for control of the injection or for termination of the injection. Injection was controlled solely on the basis of the area above the curve. All tests resulted in satisfactory sterilization. Sterilant gas was admitted into the chamber at a constant rate until an area above the curve of about 6000 units (second×Torr, see FIG. 11 wherein the injected quantity is proportional to time) was reached at which point injection was terminated and the injected pressure measured. It will be apparent from Table 2 that the injected pressure as a function of temperature, which pressure was reached on the basis of the area above the curve, is similar to that reached on the basis of the dew point as shown in Table 1.

Thus, both the dew point and the area above the curve are parameters related to condensation of the sterilant gas in the sterilization chamber and are useful for controlling the sterilization cycle to achieve reliable sterilization. Moreover, since the area above the curve is dependent on the shape of the curve, it will be readily understood that other manners of analyzing the shape of the curve, such as those discussed in the following can also be used to obtain condensation related data useful for controlling the sterilization cycle.

TABLE 2

Amount of Liquid Condensed

| TEMPERATURE (° C.) | MONITORED AREA | INJECTED PRESSURE (Torr) | DETECTED DEW POINT |
|---|---|---|---|
| 16 | 7521 | 16 | 3.6 |
| 27 | 6820 | 25.7 | 5.6 |
| 29 | 6022 | 27.8 | 5.8 |
| 36 | 6500 | 31.8 | 7.1 |

VI—Length of Tangent

Figure 13:
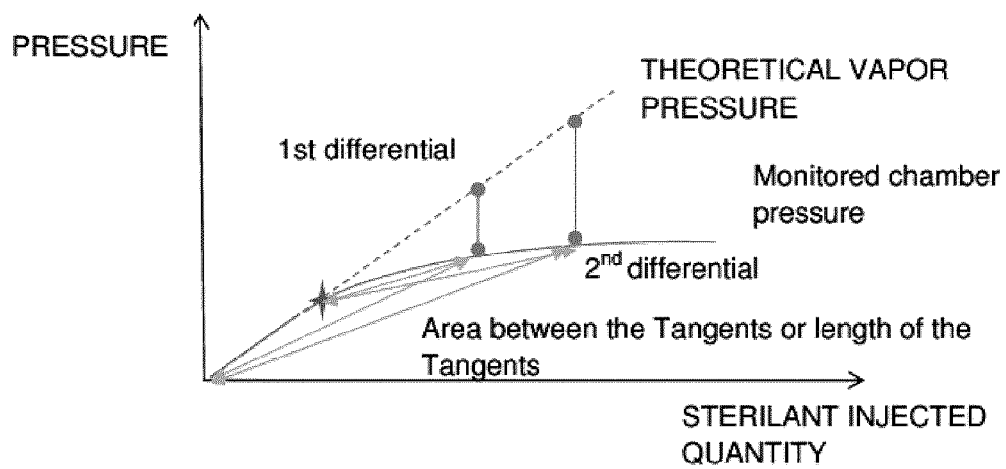
FIG. 13 illustrates a fourth method of determining a condensation related parameter.
Figure 14:
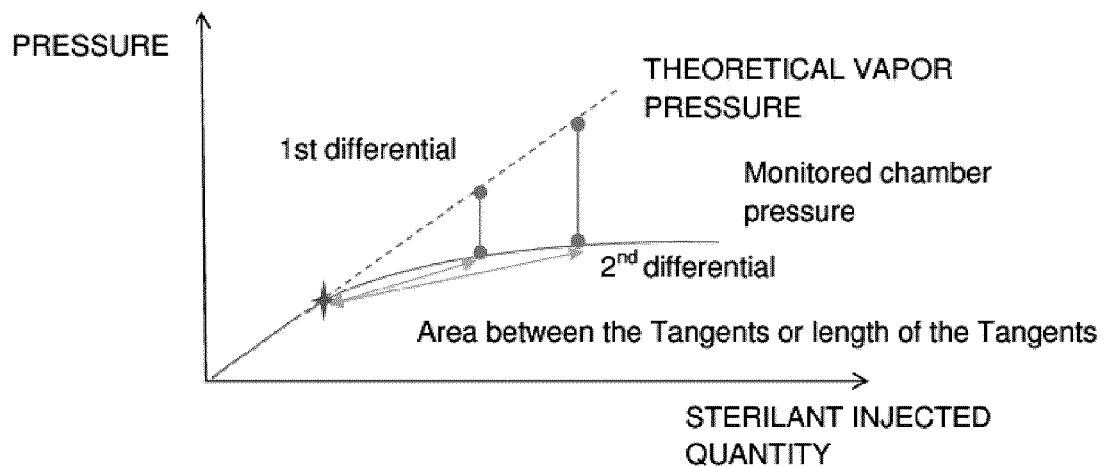
FIG. 14 illustrates a fifth method of determining a condensation related parameter.

It is also conceivable to find a tangent between the respective sections and the dew point, or the start of injection, as illustrated in FIGS. 13 and 14, and to use the length of the tangents, or the area between the tangents as better shown in FIG. 14. These tangents can then be used to set a minimum length of tangent for sterilization.

VII—Injection Curve Geometry

As it should become apparent to the skilled addressee upon reading of the present description, one can predict an ideal injection curve for the specific load for the remaining of the injection once the dew point has been detected. The wanted injection curve could be defined as a function of the types of geometry, or also as a function of the lengths of the tubes to be sterilized. The control of the speed of increase of the pressure starting from the point where the curve deviates from the theoretical curve can be used to conserve a constant speed of increase, regardless of the load. For, example, more pulses/sec can be used for large loads than for small loads, so that all surfaces experience the same increase in pressure at the same time.

As it should become apparent, a combination of two of the above described methods may be used for a particular application and/or for enhanced control.

It is also worth mentioning that a first method may be used to control the sterilization process as previously described while a second one independent to the first may be used for parametric monitoring of the efficacy of the sterilization cycle, as typically required in some European countries for example. As an illustrative example, the dew point detection may be used to control the parameters of the sterilization cycle while the area representing condensation in the chamber may be used to ensure that the sterilization cycle was correctly performed.

Sterilization Process Example

Referring to FIG. 1, an embodiment of an exemplary sterilizer for implementing a sterilization method of the invention will now be described. The sterilizer is provided with a 80 liter sterilization chamber 10, made of aluminum or stainless steel as non-limitative examples, which can be sealed to contain a vacuum. An access door 14, which can be selectively opened for access into the chamber 10, is used to seal the chamber in the closed condition. A pressure sensor 12 is preferably mounted inside the sterilization chamber 10 to monitor the chamber pressure during processing. The sterilizer also includes a hydrogen peroxide delivery unit 20 for supplying evaporated hydrogen peroxide to the sterilization chamber 10. The hydrogen peroxide delivery unit 20 is provided with an evaporator unit 22, more detailed below, which is preferably equipped with a heating device, two embedded heating elements 24, 26 in the illustrated exemplary embodiment. The heating elements 24, 26 are controlled to maintain the temperature of the hydrogen peroxide solution sufficiently high to achieve an appropriate evaporation rate and prevent freezing of the solution in the evaporator unit. The sterilizer further includes a vacuum pump 40 adapted for applying a sufficient vacuum to the sterilization chamber 10 to increase the penetration of the sterilant gas and to be able to generate evaporated hydrogen peroxide solution at the temperature inside the sterilization chamber. In a preferred embodiment, the vacuum pump 40 is adapted for producing a sufficient vacuum in the sterilization chamber 10 to lower the boiling point temperature of water in the chamber below the actual temperature of the atmosphere in the chamber. In a preferred embodiment, the vacuum pump is capable of producing a vacuum of 1 Torr (1.33 mbar). The sterilizer is also provided with a unit for destroying residual hydrogen peroxide contained in the sterilization atmosphere at the completion of the sterilization process. For example, the gas can be removed from the chamber 10 and passed over a catalytic converter 42 for a preselected time, or heated to a temperature at which sterilant gas decomposition is accelerated, for example, to 300° C. for a period of 3 seconds. Other arrangements may also be considered, for example the use of a catalytic media like a $MnO_2$ media, as known to the skilled addressee.

Figure 2:
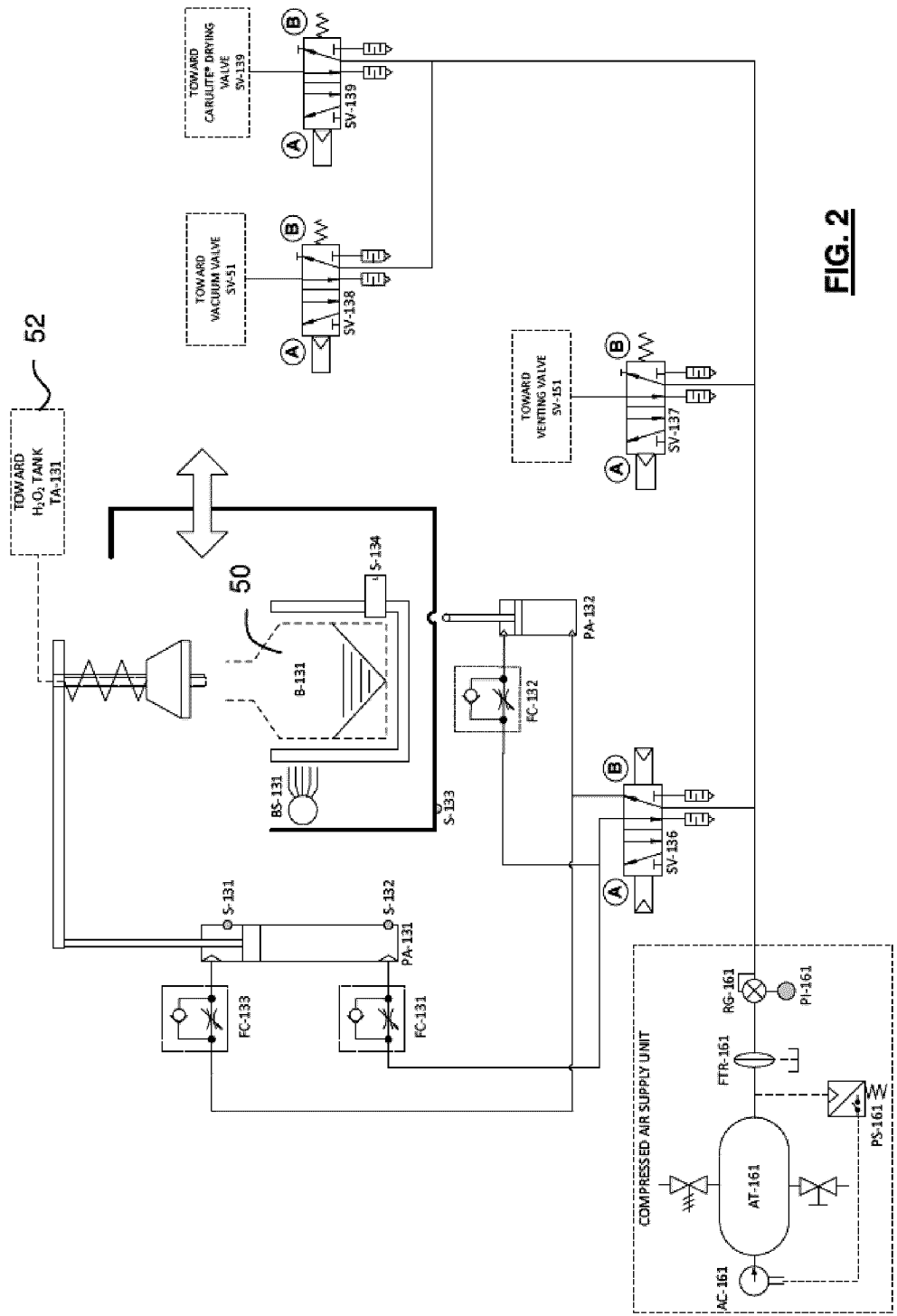
FIG. 2 is a schematic diagram of a hydrogen peroxide delivery system, according to one embodiment of the invention, the illustrated parts of the apparatus being listed in the tables of FIG. 4A and FIG. 4B.

Various configurations of hydrogen peroxide delivery unit 20 are possible, such as the two disclosed in Applicant's US patent Application No. 2011/0076192 previously referred to for non limitative examples. The delivery unit 20 depicted in the present application in FIG. 1 and FIG. 2 is mainly a bottle of hydrogen peroxide 50 connected to a buffer tank or reservoir 52. The tank 52 may be temperature controlled to limit peroxide degradation. An appropriate low level detector may also be mounted on the bottle 50 or the tank 52, as known in the art. Another configuration of the delivery unit which is not illustrated excludes the buffer tank 52. Instead, the $H_2O_2$ remains in the bottle 50 which is equipped with an appropriate low level detector and eventually an appropriate bottle temperature controlling device, as it should be apparent to the skilled addressee.

Figure 5:
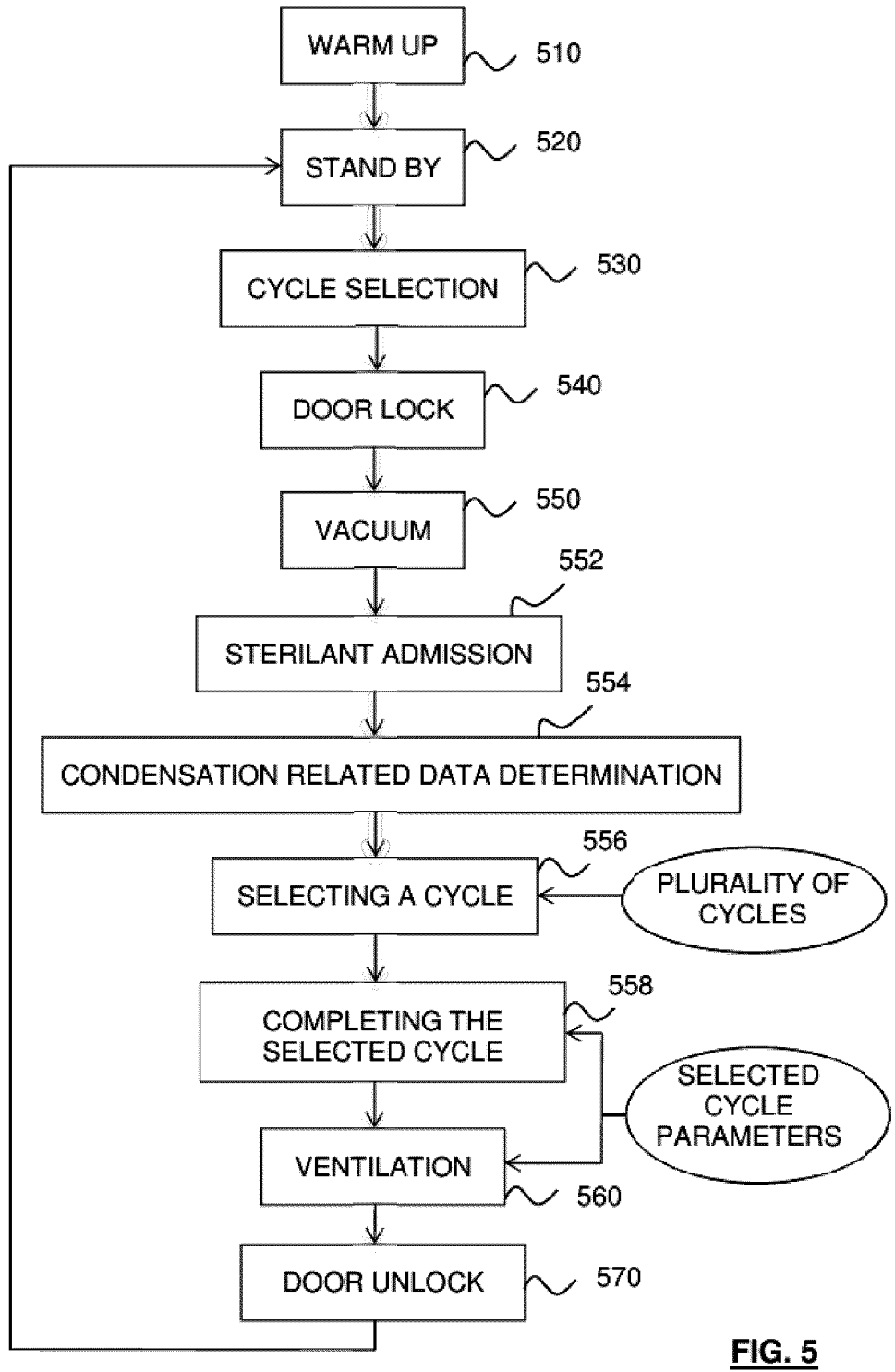
FIG. 5 is a flow diagram of a preferred sterilization method, in accordance with a first aspect of the invention.
Figure 7:
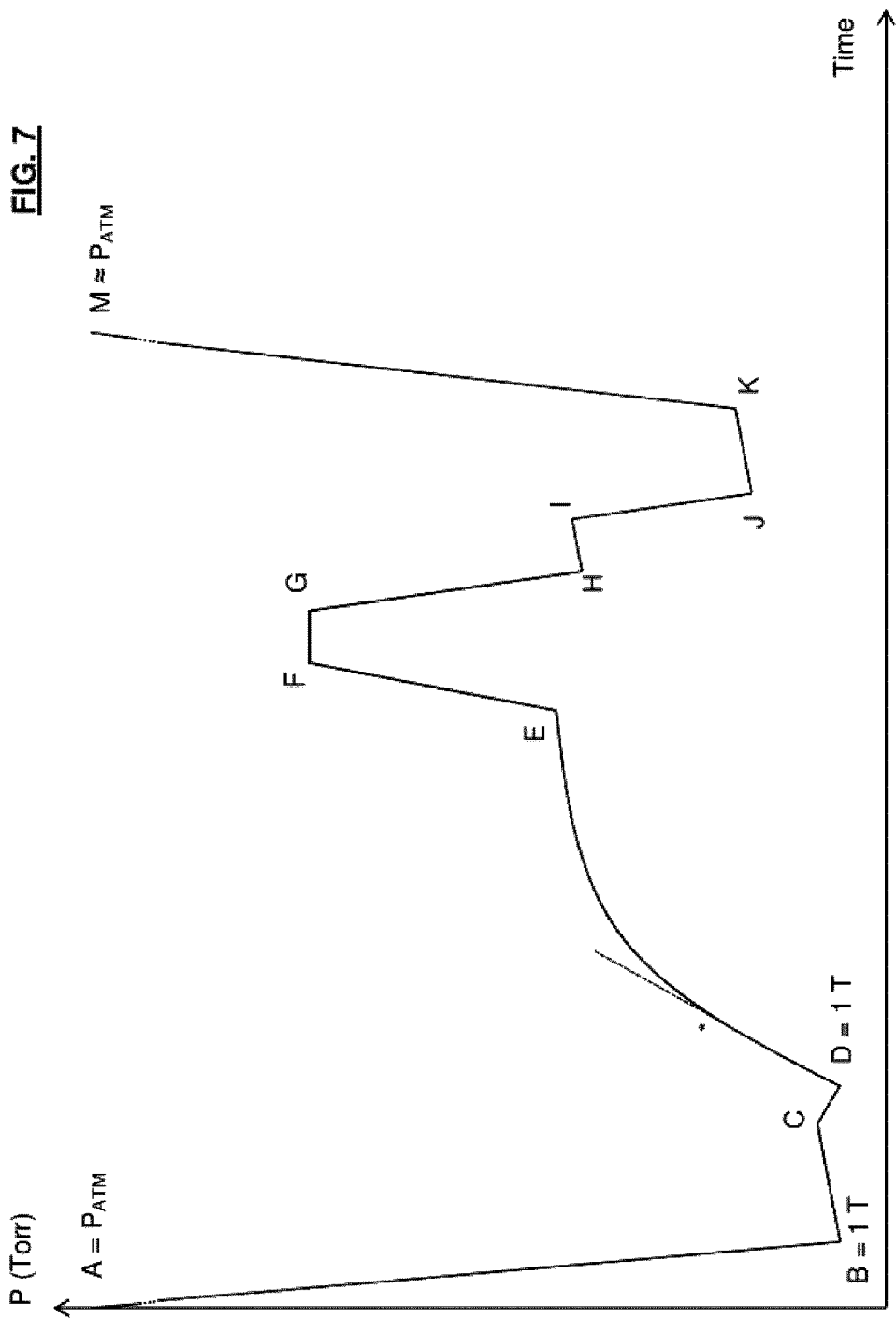
FIG. 7 is an exemplary representation of a sterilization cycle pressure profile within a sterilization chamber, in accordance with the invention.

Referring now to FIG. 5 and FIG. 7, an exemplary sterilization cycle according to the first aspect of the invention will now be described. In step 510, a warm-up of the chamber is performed. In fact, the temperature of the walls of the sterilization chamber 10 as well as the one of the evaporator unit 22 are preferably controlled throughout the sterilization process. The chamber walls are preferably kept between 40° C. and 45° C. in order to reduce sterilant gas condensation on the walls. Indeed, with this configuration, the sterilant gas will preferably condense on cooler surfaces of the load. In step 520, the articles to be sterilized are placed inside the sterilization chamber. These articles, such as medical instruments, can be placed directly into the sterilization chamber, but are preferably sealed in sterile packaging containers, sterile wraps or pouches such as generally used in the hospital environment and then placed into the sterilization chamber, as known in the art.

A cycle selection may be provided to the user in step 530, as detailed below. The chamber is then sealed in step 540 before being initially evacuated in step 550 to a first vacuum pressure sufficient to cause evaporation of the aqueous hydrogen peroxide at the temperature of the chamber atmosphere.

The vacuum in step 550 is performed in the chamber atmosphere from ambient atmospheric pressure A to sub-atmospheric pressure B, as shown in FIG. 7. Evacuation is initiated by actuating an appropriate valve mechanism between the vacuum pump and the chamber, as apparent from FIG. 1. As known in the art, ambient atmospheric pressure A may vary depending on meteorological conditions and geographical position of the sterilizer, typically from 815 Torr to 430 Torr. Tests were performed in Quebec City, Canada, where atmospheric pressure is generally around 760 Torr. Sub-atmospheric pressure B is chosen to be 1 Torr in the illustrated example but the skilled addressee will appreciate that other values typically comprised between 10 Torr and absolute vacuum may also be considered for a specific application.

The rate of evacuation (Torr/min) or the evacuation flow rate (L/min) generally depends of the chamber size, mechanical arrangements of the sterilizer and also external atmospheric conditions such as the ambient temperature and the relative humidity level. The rate of evacuation will also depend on characteristics of the load such as the material of the articles and their absorption or adsorption characteristics for example. It will also depend on actual conditions of the load, such as its temperature and its level of humidity. For example, a cold load that will contain a defined quantity of water trapped therein will generally require a longer evacuation time in order to remove such water than a load containing very little quantity of water, as it should be apparent to the skilled in the art to which the invention pertains.

Still referring to FIG. 7, when sub-atmospheric pressure B is attained, a dwell time is initiated by actuating the previously mentioned valve mechanism to separate the chamber inner atmosphere from atmospheric condition and vacuum source. This dwell time is chosen to be 3 minutes in a preferred embodiment but other values may be considered. For example, it may vary from 1 second to 10 minutes, depending on a specific application. During this time, surfaces, including complex geometry surfaces, and restricted diffusion areas, like long lumens, of the load are prepared to receive the process treatment. Indeed, air, water, humidity, absorb & adsorb media are then removed from surfaces and restricted diffusion areas of the load and allowed to evaporate (change from liquid to gas phase) in the inner atmosphere. In other words, outgassing occurs. Pressure can be maintained or may be allowed to increase as a result of vaporization. In the illustrated case, the chamber pressure is allowed to increase, as shown at point C.

Once this dwell time has been performed, a vacuum reset may be performed, as shown by point D on FIG. 7. Such a vacuum reset is optional but may be of great advantage to remove from the sterilization chamber the outgassing that occurs during the dwell time. During this step, air, water, humidity, absorbed and adsorbed media that were allowed to evaporate from the surfaces and restricted diffusion areas during the dwell time between points B and C are removed from the chamber inner atmosphere. In the illustrated case, the pressure at point D has the same value as the pressure at point B, i.e. 1 Torr, although other arrangements may be considered.

From point D, sterilant gas admission and exposure, also called Dynamic Sterilant Injection™, is initiated, as shown in step 552 of FIG. 5. As it will become apparent to the skilled addressee upon reading of the present description, sterilant gas exposure may be performed in various ways. Typically, the liquid sterilant is vaporized in a convenient manner to pass from a liquid phase to a gas phase before admission into the sterilization chamber. The gas phase of the sterilant facilitates uniformity of distribution (diffusion) into the chamber inner atmosphere to reach complex geometry and restricted areas of the articles of the load. Moreover, the vapor phase enables the sterilant gas to pass through mechanical barrier materials naturally present in instruments or in packaging materials required in terminal sterilization processes, as well known in the art.

A preferred method for admitting the sterilant gas inside the sterilization chamber is a method of the same Applicant which is described in U.S. patent application Ser. No. 13/779,193 and entitled "Hydrogen Peroxide Sterilization Method" which is incorporated therein by reference. Of course, other convenient arrangements for admitting sterilant gas inside the chamber may be considered, as it should be apparent to the skilled addressee.

In the contemplated method and as previously described, the admission of sterilant gas into the sterilization chamber is achieved by evaporation of successive pulses (doses or increments) of hydrogen peroxide solution that are then successively admitted into the sterilization chamber via an appropriate hydrogen peroxide delivery unit, as described above. The hydrogen peroxide solution pulses are preferably micro-pulses whose volume is a fixed controlled amount, and preferably comprised between 15 µl and 75 µl. As explained in the above mentioned patent application of the same Applicant, such hydrogen peroxide injection method enables to implement a controlled selective condensation of the sterilant gas onto the load, which is particularly advantageous.

In a preferred embodiment, all removal of any components in the sterilization atmosphere is stopped during admission of the sterilant gas. Moreover, the aqueous hydrogen peroxide solution is preferably evaporated and directly injected into the sterilization chamber without any measures to reduce the water vapor content. The skilled addressee will nevertheless appreciate that various modifications may be made to the sterilant gas admission without departing from the scope of the invention.

Figure 3:
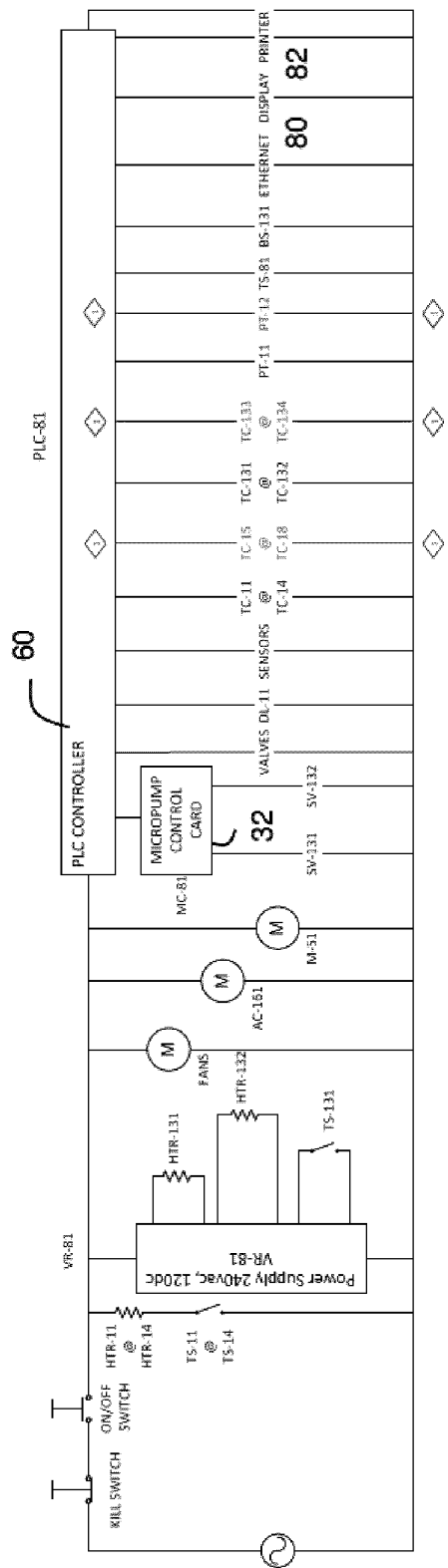
FIG. 3 is an electrical schematic diagram of the sterilization apparatus of FIG. 1, according to one embodiment of the invention, the illustrated parts of the apparatus being listed in the tables of FIG. 4A and FIG. 4B.

In one embodiment, as shown in FIG. 1, the hydrogen peroxide delivery unit 20 has two valves 28, 30 serially connected and controlled according to a pre-programmed sequence via a micro-controller 32 (See FIG. 3). The two valves 28, 30 define a passage therebetween not shown) that is operatively connected to an upstream sterilant solution supply 52 and a downstream evaporation unit 22. The evaporation unit 22 is preferably directly connected to the sterilization chamber 10 without any valve or restrictor although other arrangements may be considered. The valves 28, 30 are operated to allow a sterilant solution low to pass therethrough during a precise amount of time. Such a configuration, combined with a controlled conduit link (pipes, fittings & accessories) between the sterilant solution supply 52 and the valves 28, 30, provides the fixed controlled amount of sterilant solution to the evaporation unit 22 for each pulse to vaporize.

This controlled amount of sterilant solution (sterilant pulse) is then admitted into the evaporation unit 22. A preferred evaporation unit design consists of a heated block, preferably an aluminum block having a thermally controllable tortuous path 34 extending between an inlet 36 for receiving the controlled amount of sterilant solution and an outlet 38 for providing the evaporated sterilant solution to the sterilization chamber 10. The tortuous path 34 uses a predetermined and preselected geometry and chosen material and surface properties to control the flow properties and the heat distribution along the tortuous path. It provides for substantially complete vaporization of each dose of sterilant solution before the outlet 38 of the evaporation unit 22 while limiting any degradation of the sterilant solution. The control of the temperature of the evaporation unit 22 is executed via a PID controller driven via a PLC 60 (see FIG. 3) or an electronic interface that uses a signal value to generate an output signal. In a preferred embodiment, the temperature of the evaporation unit is maintained between about 115° C.-130° C. although other temperatures may be convenient for a particular vaporizer design. Since the outlet 38 of the evaporation unit 22 is directly connected to the sterilization chamber 10 through an appropriate tubing without any valve or restrictor, the evaporation unit is therefore subjected to the same vacuum level reached at pressure point D of FIG. 7 (or any value between D and E during the admission of the evaporated sterilant gas inside the sterilization chamber). The successive pulses are continuously injected into the sterilization chamber at a fixed rate until the end of the sterilant gas injection.

Introduction of the evaporated solution into the sterilization chamber generates an increase of the chamber pressure, initially proportional to the number of molecules introduced in the chamber's atmosphere. This proportionality is maintained until the chamber conditions are sufficient to permit a phase change from gas or vapor to liquid (condensation). This point (dew point) is identified by the star (*) symbol in FIG. 7.

As previously discussed, the conditions that cause condensation are multiple. Molecules of the evaporated solution contained in the chamber atmosphere are allowed to move freely in a chaotic manner to use up all the available internal space (maximum disorder). Molecules hit each other and in turn hit other surfaces. These contacts cause energy transfer between molecules and surfaces. Molecules at a higher energy level hitting a surface at a lower energy level will transfer a portion of their energy to the surface, resulting in an increase of temperature of the surface and a decrease in energy of the molecules (lower speed, lower temperature, lower pressure . . . ). In the same way, a lower energy level molecule that hits a surface at a higher energy level is going to gain energy, resulting in a decrease of temperature of the surface and an increase in energy of the molecule (higher speed, higher temperature, higher pressure . . . ). Molecules that are losing or gaining energy are going to take a more stable state (gaseous phase, liquid phase or solid phase) depending on the conditions where the energy transfer is taking place. Condensation is therefore the result of the energy transfer from the gaseous molecules to the surfaces where the surface properties and local atmospheric conditions cause the molecules to coalesce enough to form a liquid phase molecule package or layer.

Using a constant rate micro-pulsed injection to admit liquid sterilant solution into the evaporation unit allows for the generation of a substantially continuous flow of vapor (gas) at the outlet of the evaporation unit. Providing a pressure sensor in the sterilization chamber into which the substantially continuous flow of vapor is admitted enables monitoring of the rate of pressure increase over time (or the time required to reach a fixed increase of pressure) inside the chamber. If no condensation occurs, the rate of pressure increase is linear, following the Ideal Gas Law $PV=nRT$ (where P=chamber pressure; V=chamber volume; n=amount of moles of molecules inside the chamber; R=Gas constant; and T=Temperature of the gas). In the case wherein V, R and T are maintained constant, the pressure P should be proportional to n, so ΔP should be proportional to Δn. By maintaining Δn constant, ΔP should be constant as well. If condensation appears, then ΔP will lose its proportionality with Δn, as illustrated in FIG. 7 and FIG. 8.

Referring again to FIG. 7 and FIG. 5, and as previously mentioned, the sterilant gas admission begins at point D, step 552. This described sterilization process example uses the dew point detection method to assign optimized cycle parameters for sterilization of the specific load.

According to step 554, the dew point is detected during sterilant gas admission and then used to set a sterilant gas injection end pressure E at which sterilant gas injection is stopped. Such sterilant gas injection end pressure may be a parameter defining a cycle chosen among a predefined set, according to step 556 and as better detailed thereinafter. This pressure E is therefore dependent on the dew point being detected for the particular load being processed in the sterilization chamber. Thus, during this injection step 552, the sterilant gas is admitted inside the chamber and, from pressure identified by symbol star (*), starts to condense on various surfaces inside the chamber.

As it should become apparent upon reading of the present description, the sterilant gas injection can therefore be controlled to tailor or adapt the sterilization process to any load conditions to thereby provide optimal conditions (including the amount of condensation present on the load) enabling to achieve/enhance the target level of sterilization of the specific load.

Tests have been performed for different load compositions at different load temperatures to empirically determine the optimal sterilant gas injection end pressure E, as shown in Table 1 above. In a preferred non-limitative embodiment and according to step 556, sterilant gas injection end pressure E ranges from 13 Torr to 35 Torr for a load temperature ranging from 18° C. to 30° C. The total injection time, between points D and E depends on various parameters and also on the load conditions (temperature, size, type of medical instruments), but generally lasts several minutes. As non-limitative typical examples, total injection time may range from 4 to 10 minutes with the 80 liter sterilizer described herein.

Once sterilant gas injection has been stopped, at point E in FIG. 7, and according to step 558, the injection cycle is completed. In the illustrated example, a pressure push is implemented. The pressure push consists of introducing a compression gas in the chamber's atmosphere to force molecules to reach restricted areas and complex geometries of medical devices, as detailed in U.S. Pat. No. 5,527,508 entitled "Method of enhanced penetration of low vapor pressure chemical vapor sterilants during sterilization" which is incorporated by reference herein. A gas (such as air, HEPA filtered air, ozone, oxygen, inert gas or any other gas or vapor, but air preferably) is introduced by actuating a valve mechanism between a gas source (ambient atmosphere in our case) and the sterilization chamber. The rate of fill (Torr/min) and flow rate (L/min) are a function of the chamber size, mechanical component selection (diameter of the air inlet for example) and actual conditions (temperature, humidity level, electrical supply . . . ). The compression gas introduction increases the chamber pressure from E up to a pressure F. In one embodiment, we empirically choose F=E+35 Torr (fixed); i.e., F ranges between 48 and 70 Torr. In other words, F is a fixed amount (ΔP) from E to F. In an alternative embodiment, it could also be considered to use a fixed pressure F, for example 50 Torr or any value above that that will enable to conveniently force sterilant gas into the restricted areas. In yet another embodiment, the pressure push may also be time-controlled. In other words, the pressure increase generated by the introduction of the compression gas may be controlled via a fixed period of time. During this step, the sterilant gas condenses even further on the surfaces inside the chamber and further contributes to inactivate microorganisms.

Following the pressure push E-F, an upper pressure dwell time is initiated by actuating the appropriate valve mechanism to separate the chamber's atmosphere from the compression gas source, i.e. the ambient atmosphere. In a preferred embodiment, the upper pressure dwell time is chosen to be 30 seconds, but other values may be suitable, for example from a few seconds to several minutes. During this time, it is believed that the ambient conditions inside the sterilization chamber become more stable and/or reach equilibrium. It is also believed to enhance killing efficacy for long restricted areas such lumens and also complex geometrical surfaces. During this step, pressure may naturally react, i.e. slight increase or decrease, to the conditions of the chamber's atmosphere, including the load characteristics. In an alternative embodiment, the pressure inside the chamber may be controlled to remain constant through actuation of the corresponding evacuation valve.

Still referring to FIG. 7, dwell time F-G is followed by a controlled evacuation of the chamber according to the method described in U.S. Pat. No. 5,804,139 entitled "Two-step sterilization process using liquid sterilant" which is herein incorporated by reference. As will become apparent below, this controlled evacuation (step 558 of completion of the cycle in FIG. 5) is devised to achieve a target sterility of surface areas in a first step, as well as diffusion restricted areas such as the interior surfaces of long lumens in a subsequent step.

A first sterilant gas evacuation, illustrated as G-H, is initiated. The rate of evacuation (Torr/min) and flow rate (L/min) depend on various conditions, mechanical and load related conditions especially, as detailed above with reference to the initial vacuum. Evacuation is performed from G to a lower pressure H, generally comprised between G and 20 Torr, but typically between 22 Torr and 32 Torr. As detailed in previously cited U.S. Pat. No. 5,804,139, this step consists of bringing the pressure of the chamber to a predetermined pressure range at which a portion of liquid (condensed) sterilant is vaporized from the non-diffusion restricted area.

Although pressure H may be chosen to be a fixed level of 22 Torr for example in a first embodiment, this pressure may be adjusted to a predetermined level, in accordance with the previous dew point detection. Indeed, in an alternative embodiment, this pressure H may be empirically determined through testing at various dew point detection levels, as further detailed below.

Once the first sterilant evacuation has been performed, an intermediate pressure dwell H-I that may vary from few seconds to 10 minutes, but typically between 30 seconds and 3 minutes is then initiated. During this time, new ambient conditions equilibrate inside the chamber. In fact, since the selected pressure H is typically above the vapor pressure of the sterilant at the specific temperature, most of the evacuation chamber atmosphere removed during the first evacuation is water. Then, a portion of the water of the sterilant solution that was condensed on the load has been removed from the chamber, thereby providing a microlayer of more highly concentrated sterilant on the load surfaces. This dwell time allows the sterilant to react with the remaining microorganisms which have resisted up to this point in the sterilization process. As shown in the illustrated graph, pressure is allowed to naturally react, i.e. increase, to the conditions of the chamber's atmosphere although it may alternatively be maintained at a constant pressure H. As it should become apparent, the dew point detection may be used to determine the length of this dwell time instead of using a fixed time.

A second sterilant evacuation I-J is then initiated, as previously explained. Evacuation is performed from pressure I to a lower pressure J, generally comprised between 20 Torr and 1 Torr, but more typically between 8 Torr and 1 Torr. This step consists of bringing the pressure of the chamber to a lower pressure range at which a portion of the liquid (condensed) sterilant is vaporized from the diffusion restricted areas. In a preferred embodiment, pressure J is adjusted to a pre-determined level according to the previously detected dew point inside the chamber, as detailed below. It is believed that this further contributes to inactivate any remaining microorganisms.

A lower pressure dwell time J-K is initiated, as previously explained. This dwell time may vary from few seconds to 10 minutes but 1 to 3 minutes may be appropriate for medical devices having very long lumens and/or very hard to reach places. During this time, which may also be dynamically determined according to the dew point detection, complex geometrical surfaces (such as long restrictive areas like lumens) inside the chamber are stabilized to the new chamber conditions. This dwell time allows the sterilant gas to react with any remaining microorganisms which have resisted sterilant gas attack up to this point. During this dwell time, the pressure may naturally readjust, i.e. increase, to the conditions of the chamber's atmosphere, or alternatively, be controlled to remain at the chosen value.

At this point, targeted sterilization of the load is achieved and the chamber can be returned to atmosphere by introducing a gas therein. A gas (such as air, HEPA filtered air, ozone, oxygen, inert gas or any other gas or vapor, preferably air) is introduced by actuating the appropriate valve mechanism, as previously described. Pressure is increased from K up to substantially atmosphere M since it is preferred for safety considerations to remain slightly below the actual atmospheric pressure. During this step, the introduced gas comes in contact with surfaces inside the chamber and helps in removing residual liquid or gaseous sterilant.

To remove all remaining liquid or gaseous sterilant from the sterilization chamber a ventilation phase 560 (see FIG. 5) may be started, which preferably includes multiple cycles of evacuation of the chamber and flushing with air or other appropriate gas, as known in the art. For non-limitative examples, oxygen, nitrogen, ozone or argon may be conveniently used. After the ventilation phase 560, the door is unlocked in step 570 and the sterilized articles can be safely taken from the chamber.

In a preferred embodiment, as previously mentioned, the complete sterilization process consists of a cycle similar to the one described above that is repeated twice for regulatory purposes. In other words, when pressure inside the chamber reaches pressure M, a vacuum is performed in the chamber, as the one performed between A-B and another sterilant gas admission and evacuation is begun before the final ventilation phase is performed. In a preferred embodiment of the ventilation phase, a vacuum is initiated, preferably to 1 Torr, although others values up to 10 Torr for a non-limitative example may be considered. A deep vacuum of 1 Torr is highly preferred to reach a pressure level at which remaining condensed sterilant gas trapped in the load is forced into the vapor state. This operation is also used to lower the residual liquid sterilant on device surfaces. Air, water, humidity, absorbed and adsorbed products are removed from the surfaces and complex geometries in this step.

Still in the preferred embodiment, a dwell time followed by a vacuum reset is implemented before flushing the chamber with air. The dwell time may last from 1 second to several minutes but a one minute dwell time is preferred. Air, water, humidity, absorbed and adsorbed products are allowed to evaporate in the chamber's atmosphere. This operation is also advantageous to further lower residual liquid sterilant on load surfaces. The pressure inside the chamber naturally reacts to the conditions of the chamber's atmosphere and outgassing occurs. A vacuum reset is then performed to remove products that have previously evaporated during the dwell time.

The ventilation phase may comprise successive evacuation and flushing steps as previously described to help removal of residual liquid sterilant. As previously mentioned, the number of ventilations performed as well as other related parameters may be dynamically determined during the processing cycle, in accordance with the previously detected dew point. Of course, different vacuum pressures, dwell times and number of repetitions can be used, as long as the desired liquid or gaseous sterilant removal is achieved. For a non-limitative example, the number of ventilations may be determined in accordance with the sterilant gas quantity that has been injected. During the process, the gas mixture evacuated from the sterilization chamber 10 is passed over the hydrogen peroxide destroying unit prior to be released to the atmosphere to ensure a complete decomposition of the liquid or gaseous sterilant.

Once atmospheric pressure is reached after the last flushing step, the door mechanism of the sterilization chamber is actuated to permit access to the load.

In yet a further embodiment, an optional third sterilant evacuation may be implemented after the dwell time J-K and before the return to atmosphere, as detailed in previously cited U.S. Pat. No. 5,804,139. Typically, the pressure level of this optional third sterilant evacuation may range from 1 Torr to 5 Torr but 1 Torr is preferred. As mentioned in this patent, bringing the pressure to this low level may help to remove residual liquid or gaseous sterilant and/or enhance sterilization efficacy.

Figure 6:
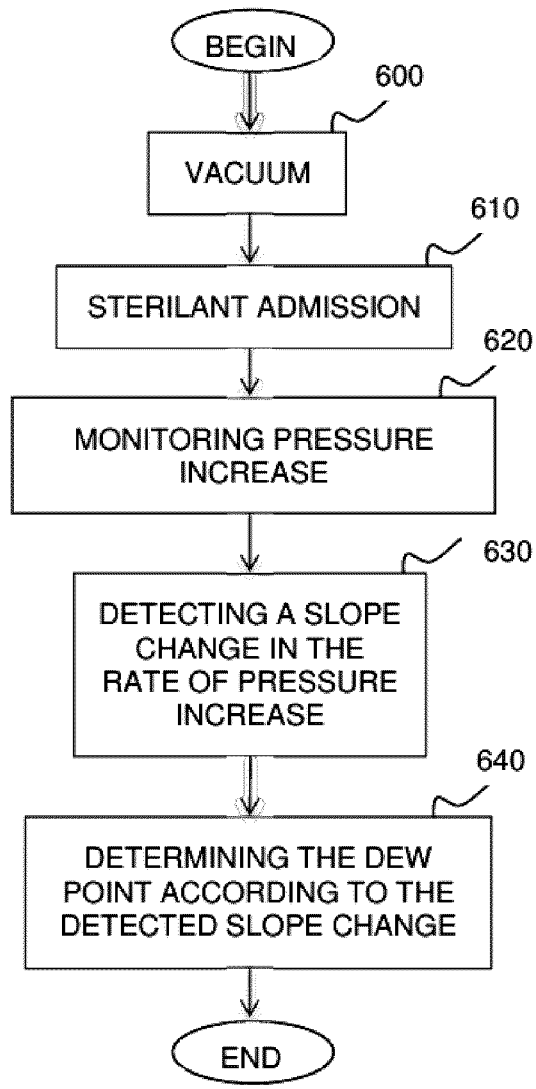
FIG. 6 is a flow diagram of a preferred method for determining a dew point in a sterilization chamber according to load conditions, in accordance with a second aspect of the invention.

Referring now to FIG. 6, a method for determining a dew point in a sterilization chamber according to load conditions will now be described in accordance with a preferred embodiment of the invention. As previously described, in a preferred embodiment, after step 600 of applying a vacuum inside the chamber. sterilant gas is admitted in the sterilization chamber in step 610, preferably by evaporating repeated equal pulses or increments of sterilant solution at a constant pulse rate and at a pulse volume sufficient for controlling selective condensation of sterilant gas, the sterilant solution pulse volume being preferably lower than 75 µl as previously described.

The pressure inside the sterilization chamber is monitored before the beginning of the sterilant gas injection and during the injection, according to step 620. A chamber pressure slope (sec/torr), or an elapsed time per pressure increment, is then calculated, preferably in intervals, for example using a delta pressure from initial chamber pressure divided by time elapsed from the beginning of the sterilant gas admission. In others words, the pressure increase inside the chamber during sterilant gas admission is monitored for detecting a slope change in the rate of pressure increase. The rate change detected in step 630 will be used to determine the dew point in the sterilization chamber, according to step 640, as it should become more apparent below.

According to one embodiment, a table of predetermined pressure rate ranges, also called ratio Ri as shown in Table 3 below is created. This table will first be used to determine the steepness or angle of the chamber pressure slope for a period of sterilant gas admission before condensation occurs in the chamber. The chamber pressure rate (slope) is continuously monitored and compared every 0.2 second during the time from at least the beginning of the sterilant gas admission and until a predetermined pressure above all dew points expected for any type of load is reached.

TABLE 3

| Ratio range $R_i$ | Recurrence $N_i$ | Recorded pressure $P_i$ | Parameter set #1 $PS_{i,j}$ | Parameter set #2 $PS_{i,j+1}$ | ... | Parameter set #j $PS_{i,m}$ |
|---|---|---|---|---|---|---|
| $R_1$ | $N_1$ | $P_1$ | $PS_{1,1}$ | $PS_{1,2}$ | ... | $PS_{1,m}$ |
| $R_2$ | $N_2$ | $P_2$ | $PS_{2,1}$ | $PS_{2,2}$ | ... | $PS_{2,m}$ |
| ... | ... | ... | ... | ... | ... | ... |
| $R_i$ | $N_i$ | $P_i$ | $PS_{n,1}$ | $PS_{n,2}$ | ... | $PS_{n,m}$ |

Each ratio range Ri is predefined as follows:

$$\left[\frac{\Delta t}{\Delta P_{low}}, \frac{\Delta t}{\Delta P_{high}}\right]$$

where $\Delta t$ is the time elapsed since the beginning of sterilant gas admission and $\Delta P$ is the pressure differential since the beginning of sterilant gas admission. The number of ratio ranges Ri may be any convenient chosen value but 12 ranges for example may be suitable. In one example, R1 may be chosen to be 0-3.5 sec/Torr, R2 may be chosen to be 3.5-3.7 sec/Torr and R12 may be chosen to be 7.0-10.0 sec/Torr. The last range set Rn is excluded from selection and is specifically chosen to be large enough in order to store out of interest data corresponding to the end of the injection where condensation has already occurred. As it should become apparent below to the skilled addressee, the set of Ri will be used to characterize the pressure increase inside the chamber during sterilant gas admission.

At each fixed time interval, the monitored rate value is compared to the pre-determined interval sets Ri. If the rate value fits in a specific interval, a recurrence Ni of this event is added into an associated memory slot and the actual chamber pressure value Pi is recorded in another associated memory slot, as detailed below. In other words, for each fixed $$\Delta t, \frac{\Delta r}{\Delta P}$$

is calculated and compared to the available ranges Ri. For the corresponding Ri, Ni=Ni+1 and Pi=monitored pressure.

When chamber pressure reaches a predetermined pressure known to be above the dew point of the chamber, 12 Torr for example, the value of "Recorded pressure" corresponding to the line with higher number of occurrences in column "Recurrence Ni" is used as input data characterizing the chamber pressure reference where condensation has not yet started in the chamber. In other words, the chamber pressure slope is decreasing from this point and condensation inside the chamber begins to occur.

In the described embodiment, the chamber pressure slope (sec/torr) is calculated at intervals using a delta pressure from the initial chamber pressure divided by time elapsed from the beginning of the sterilant gas admission but the skilled addressee will appreciate that various alternatives may be used. For example, other pressure windows or even a dynamic window may be considered. Moreover, any other convenient methods permitting detection of the inflection point in the pressure vs time curve could also be considered. Specially designed tools or software to detect the inflection point could be used. Abacus or charts of known sterilant gas injection patterns may also be used for comparison, as it should become apparent to the skilled addressee.

As previously explained with reference to FIG. 5 and FIG. 7, the determined chamber pressure at the dew point may then be used as a data source to determine various sterilization cycle parameters, such as the dynamic sterilant gas injection end pressure E in using Parameter set #1 $PS_{i,j}$ and the second sterilant evacuation pressure set point J in using Parameter set #2 $PS_{i,j+1}$ in Table 3, these values having been empirically determined through testing. In this example and as previously explained, sterilant injection is stopped when the monitored pressure in the chamber reaches the dynamic sterilant injection pressure set point, in addition to the initial pressure, 1 Torr in our example.

In one illustrative example, the extracted pressure is 3.2 Torr. The dynamic sterilant injection delta pressure set point is set at 15 Torr. Since the initial chamber pressure at vacuum is 1 Torr, the sterilant injection step is completed when the pressure in the chamber reaches 16 Torr. In a similar manner, for an extracted pressure of 3.2 Torr, the second sterilant evacuation pressure set point J is set at 2 Torr. These values have been empirically predetermined through testing of defined loads and are given as an illustrative example only.

The empiric set point J may be determined through monitoring of the chamber atmosphere in various tests. For example, a UV detector, infrared spectroscopy or any other convenient tool may be used to provide data related to the concentration of the vaporized sterilant inside the chamber. Such technique may also be used in the case where pressure H is also dynamically determined during the sterilant admission, as it should be apparent to the skilled addressee.

As previously explained, other alternative methods may be used to monitor other condensation related parameters. For example, a sensor measuring formation of a micro-layer of condensate inside the chamber may be used. Another specially designed sensor enabling to monitor the thickness and/or sterilant concentration of such a micro-layer on the load surfaces may also be considered.

As it should now be apparent to the skilled addressee, each and every parameter of the sterilization cycle may be specifically determined during the sterilant admission according to the detected condensation related data to thereby provide a selected cycle adapted for the load under process. The skilled addressee will appreciate that the cycle may be completely tailored according to the specific conditions of the load, including its temperature and composition. This allows processing of a wide range of load temperatures, ranging from example from 16° C. to 37° C., without requiring any prior conditioning of the load. The quantity of sterilant that is used may also be specifically adapted to the load under processing. This may enable to reduce operating costs and processing time while enhancing instrument compatibility.

Referring again to FIG. 5, in accordance with one embodiment, the user has the choice of multiple different sterilization cycles. In a preferred method, the user can choose in cycle selection step 530 of the process among a plurality of predetermined frame cycles adapted for specific load characteristics. For example, an express cycle may be implemented for less challenging loads. Others cycle frames specifically directed to loads including rigid endoscopes only or flexible endoscopes only may also be provided.

Thus, the selected cycle frame to perform may firstly be selected by the user among a plurality of cycle frames, in accordance with the type of load to process. Then, each parameter of the selected cycle may be automatically determined during the sterilant admission according to the specificities of the load.

Once the user has chosen one of the proposed cycles, the user closes the sterilization chamber door and pushes the start button. The sterilizer control system (see FIG. 3) will then, under the control of a built-in operating software, start the sterilization process according to the cycle chosen and using preselected parameters for the cycle chosen.

Referring now to FIG. 3 and FIG. 4, in one embodiment, the sterilization apparatus is preferably controlled by a control system built around a PLC shelf 80 (Programmable Logic Controller). This shelf contains a power supply, a CPU unit, a Device Net Transceiver, a 24 Volt DC discrete input module, a 120 VAC discrete output module, a transistor discrete output module and an RS232C communication module, as known in the art. All those modules are stacked together by an intrinsic connecting system that contains a data and address bus. The Device Net Transceiver is used to communicate in full duplex, the data between the CPU and various converters.

The control system is provided with a user interface which, in a preferred embodiment, includes a touch-sensitive liquid crystal display (LCD) screen 80, a printer 82 for performance reports and a communications port (Series RS-232) allowing the user to receive and transmit information necessary for use of the apparatus. It will be readily apparent to the person skilled in the art that other types of user interfaces can be used such as touch-sensitive pads, keyboards, or the like, and other types of communications interfaces.

In the preceding description, for purposes of explanation, numerous details are set forth in order to provide a thorough understanding of the embodiments of the invention. However, it will be apparent to one skilled in the art that these specific details are not required in order to practice the invention.

What is claimed is:

1. A method for sterilizing a load in a sterilization chamber under vacuum, comprising the steps of:
    admitting a sterilant gas into the sterilization chamber under vacuum;
    during admission of the sterilant gas monitoring a sterilant condensation related parameter in the sterilization chamber;
    determining a value of the sterilant condensation related parameter, either upon the occurrence of condensation, or at the onset of condensation;
    selecting a sterilization cycle among a plurality of predetermined sterilization cycles according to the value of the condensation related parameter; and
    performing the selected sterilization cycle for sterilizing the load, wherein the sterilant gas is admitted at a constant rate and the sterilant condensation related parameter is the chamber pressure.

2. The method of claim 1, wherein the sterilant condensation related parameter is dependent on a condition of the load.

3. The method of claim 1, wherein one of the occurrence of condensation and the onset of condensation is detected by monitoring for a change in a rate of pressure increase in the sterilization chamber during admission of the sterilant gas.

4. The method of claim 3, wherein the sterilization cycle is chosen based on the pressure in the chamber at the point in time where the change in the rate of pressure increase is detected.

5. The method of claim 1, comprising the further step of evaporating a liquid sterilant to generate the sterilant gas.

6. The method of claim 5, wherein the liquid sterilant is an aqueous sterilant solution and the step of evaporating includes completely evaporating both sterilant and solvent to generate a water vapor and sterilant gas mixture prior to the admitting step, optionally the liquid sterilant is an aqueous solution of hydrogen peroxide and the sterilant gas is hydrogen peroxide gas.

7. The method of claim 1, wherein the sterilant gas is hydrogen peroxide gas.

8. A method for sterilizing a load in a sterilization chamber under vacuum, comprising the steps of:
    admitting a sterilant gas into the sterilization chamber under vacuum;
    during admission of the sterilant gas monitoring a sterilant condensation related parameter in the sterilization chamber;
    determining a value of the sterilant condensation related parameter, either upon the occurrence of condensation, or at the onset of condensation;
    selecting a sterilization cycle among a plurality of predetermined sterilization cycles according to the value of the condensation related parameter; and
    performing the selected sterilization cycle for sterilizing the load, wherein the sterilant condensation related parameter comprises a quantity of condensed sterilant gas.

9. The method of claim 8, wherein the sterilant gas is provided at a constant rate and the quantity of condensed sterilant gas is determined by calculating an area between a theoretical vapor pressure curve of the sterilant gas and an actual vapor pressure curve based on measured chamber atmosphere parameters, the area representing a measure for the quantity of condensed sterilant gas.

10. The method of claim 8, wherein the sterilant gas is hydrogen peroxide gas.

11. A method for sterilizing a load in a sterilization chamber under vacuum, comprising the steps of:
    admitting a sterilant gas into the sterilization chamber under vacuum;
    during admission of the sterilant gas monitoring a sterilant condensation related parameter in the sterilization chamber;
    determining a value of the sterilant condensation related parameter, either upon the occurrence of condensation, or at the onset of condensation;
    selecting a sterilization cycle among a plurality of predetermined sterilization cycles according to the value of the condensation related parameter; and
    performing the selected sterilization cycle for sterilizing the load, wherein the sterilant condensation related parameter comprises a ratio of an amount of condensed sterilant gas to a total amount of injected sterilant gas.

12. The method of claim 11, wherein the sterilant gas is provided at a constant rate, the amount of condensed sterilant gas is determined by calculating an area between a theoretical vapor pressure curve of the sterilant gas and an actual vapor pressure curve based on measured chamber atmosphere parameters, the area representing a measure for the quantity of condensed sterilant gas.

13. The method of claim 11, wherein the sterilant gas is hydrogen peroxide gas.

14. A method for sterilizing a load in a sterilization chamber under vacuum, comprising the steps of:
admitting a sterilant gas into the sterilization chamber under vacuum;
during admission of the sterilant gas monitoring a sterilant condensation related parameter in the sterilization chamber;
determining a value of the sterilant condensation related parameter, either upon the occurrence of condensation, or at the onset of condensation;
selecting a sterilization cycle among a plurality of predetermined sterilization cycles according to the value of the condensation related parameter; and
performing the selected sterilization cycle for sterilizing the load, wherein the selecting a sterilization cycle comprises determining a final quantity of sterilant gas to inject.

15. The method of claim 14, wherein the sterilant gas is hydrogen peroxide gas.

16. A method for sterilizing a load in a sterilization chamber under vacuum, comprising the steps of:
admitting a sterilant gas into the sterilization chamber under vacuum;
during admission of the sterilant gas monitoring a sterilant condensation related parameter in the sterilization chamber;
determining a value of the sterilant condensation related parameter, either upon the occurrence of condensation, or at the onset of condensation;
selecting a sterilization cycle among a plurality of predetermined sterilization cycles according to the value of the condensation related parameter; and
performing the selected sterilization cycle for sterilizing the load, wherein the selecting a sterilization cycle comprises determining a predetermined sterilant gas injection end pressure.

17. The method of claim 16, wherein the sterilant gas is hydrogen peroxide gas.

* * * * *